(12) United States Patent
Pedersen

(10) Patent No.: US 9,636,520 B2
(45) Date of Patent: May 2, 2017

(54) PERSONALIZED LIGHTING CONTROL

(71) Applicant: LIGHTEN APS, Regstrup (DK)

(72) Inventor: Steen Hvidtfeldt Hessellund Pedersen, Jyllinge (DK)

(73) Assignee: LIGHTEN APS, Regstrup (DK)

( * ) Notice: Subject to any disclaimer, the term of this patent is extended or adjusted under 35 U.S.C. 154(b) by 638 days.

(21) Appl. No.: 14/064,407

(22) Filed: Oct. 28, 2013

(65) Prior Publication Data
US 2014/0052220 A1     Feb. 20, 2014

Related U.S. Application Data

(63) Continuation-in-part of application No. PCT/DK2012/050141, filed on Apr. 27, 2012.

(30) Foreign Application Priority Data

| | | |
|---|---|---|
| Apr. 28, 2011 | (DK) | 2011 70206 |
| Dec. 14, 2011 | (DK) | 2011-70710 |
| Apr. 23, 2013 | (EP) | 13164906 |

(51) Int. Cl.
*A61B 19/00*     (2006.01)
*A61N 5/06*     (2006.01)

(52) U.S. Cl.
CPC .... *A61N 5/0618* (2013.01); *A61N 2005/0642* (2013.01); *A61N 2005/0652* (2013.01); *A61N 2005/0665* (2013.01)

(58) Field of Classification Search
CPC .. A61N 5/0613; A61N 5/0618; A61N 5/0622; A61N 2005/0652;
(Continued)

(56) References Cited

U.S. PATENT DOCUMENTS

2005/0015122 A1\* 1/2005 Mott ................. A61M 21/00
607/88
2007/0138978 A1 6/2007 Rains, Jr. et al.
(Continued)

FOREIGN PATENT DOCUMENTS

| WO | WO2008/146219 | 12/2008 |
|---|---|---|
| WO | WO2009/044330 | 4/2009 |

OTHER PUBLICATIONS

International Search Report on corresponding PCT application (PCT/DK2012/050141) from International Searching Authority (EPO) dated Nov. 23, 2012.
(Continued)

*Primary Examiner* — Ahmed Farah
(74) *Attorney, Agent, or Firm* — Klein, O'Neill & Singh, LLP

(57) ABSTRACT

A lighting system for initiating change in a mammal's circadian or well-being state includes a computational unit configured to receive state information regarding the mammal's circadian or well-being state, and operational information from a light sensor with spectral and luminosity sensitivity. The computational unit is configured to compare the operational information with the state information, and on the basis of this comparison, the computational unit outputs a control signal to a light control unit which, in turn, adjusts a controllable light source to vary its light output so as to initiate the desired change in the mammal's circadian or well-being state.

24 Claims, 24 Drawing Sheets

(58) Field of Classification Search
CPC .... A61N 2005/0654; A61N 2005/0626; A61N 2005/0627; A61N 2005/0628
USPC ...................................... 607/88–91; 128/898
See application file for complete search history.

(56) References Cited

U.S. PATENT DOCUMENTS

| | | |
|---|---|---|
| 2007/0273290 A1 | 11/2007 | Ashdown et al. |
| 2008/0091250 A1* | 4/2008 | Powell ................. A61M 21/00 607/90 |
| 2011/0084614 A1 | 4/2011 | Eisele et al. |
| 2013/0138182 A1* | 5/2013 | Nissila ................. A61N 5/0618 607/88 |
| 2015/0022093 A1* | 1/2015 | Smith ................. A61N 5/0618 315/151 |
| 2015/0105701 A1* | 4/2015 | Mayer ................. A61M 16/14 601/3 |

OTHER PUBLICATIONS

Written Opinion on corresponding PCT application (PCT/DK2012/050141) from International Searching Authority (EPO) dated Nov. 23, 2012.
European Search Report on corresponding EP application (13164906.3) dated Sep. 4, 2013.
Helson H et al.; "The role of spectral energy of source and background color in the pleasantness of object colors"; Applied Optics; vol. 9, No. 7, pp. 1513-1562; Jul. 1, 1970; XP002712228.

* cited by examiner

PERSONALIZED LIGHTING CONTROL

CROSS-REFERENCE TO RELATED APPLICATIONS

This application is a Continuation-in-Part of International Application No. PCT/DK2012/050141, filed Apr. 27, 2012. The application further claims priority under 35 U.S.C §119(a) from European Application No. 13164906.3, filed Apr. 23, 2013. The disclosures of both of these prior-filed applications are incorporated herein by reference in their entireties.

BACKGROUND

The present disclosure relates to a lighting system for initiating change of a mammal's circadian state or wellbeing.

Productivity of humans and in general mammals is essential to the industrial world and the wellbeing of human kind. Optimizing the way that humans and generally mammals use their resources is essential to enable humans and mammals to perform more effectively. As such, machinery and better procedures have proven beneficial to human kind.

It is well known that the society has organized itself with around a generally fixed work schedule for production of all sorts. However, it is known that individuals each have an individual chronotype or circadian type defining a rhythm that, in most cases, will be more or less out of synch with the scheduled working hours.

Besides aiding efficiency during a work schedule, it is also recognized that lighting conditions can improve the overall well-being experienced by the individual user. Such improved well-being can lead to further increased efficiency or output. Usually lamps or light sources are designed to provide light that enables a human or mammal to see objects. This happens by providing a light source that emits a spectrum that directly or via reflections excites photoreceptors, specifically, rods and cones, contained in the retina. Hence an image formed on the retina by the lens in the eye results in the rods and cones transmitting signals to the brain carrying information about the shape and color of what is seen. This process occurs essentially instantaneously.

In addition, the retina also has a third photoreceptor: the photosensitive ganglion cell, the photosensitive Retinal Ganglion Cells (pRGC), or intrinsically photosensitive Retinal Ganglion Cells (ipRGC). Unlike the other receptors, the pRGC respond to light over time or in a cumulative fashion, and the pRGC are not image-forming. The pRGC provide the brain information about the ambient light intensity and colour.

Although some technological efforts have been made to create a workable "circadian pacemaker," these efforts have been overly complex, impractical to implement or systems that have been limited to certain situations.

One such lighting system is disclosed in patent application US 2005/0015122. The publication discloses a method and a system applying a model based predictive control techniques and variations thereof using optimization schemes based on cost functions and mathematical models such as the Jewett-Kronauer model of the circadian cycle. However, control signals used in the system focus on the light intensity and are deficient with respect to the use of colors. Moreover, the control signals are focused on returning a subject "to a natural phase" and are deficient with respect to boosts of energy for the well-being of a subject. Also, the disclosed system and control signals do not provide any insight into how to make a functioning lighting environment that can be implemented as an ordinary lighting system in rooms in private homes, offices, factories, or hospitals for example. Also, the system and control signals disclosed do not provide any insight into how a light source can be configured to provide a variable color, and, in particular, the disclosed system and control signals do not provide any insight into how the color and intensity can be varied essentially continuously either individually or together. Finally, the system and control signals disclosed do not provide any insight into how to reduce power consumption and subsequently $CO_2$ emissions.

SUMMARY

It is an object of this disclosure to provide a system that overcomes any of the mentioned shortcomings of mentioned prior art.

Broadly, a system according to the present disclosure comprises at least one computational unit with memory, a processor, at least one input and at least one output. Further, the lighting system comprises at least one light sensor with spectral and luminosity sensitivity and is configured to provide information through a connection to said least one input of the computational unit, wherein the computational unit is configured to collect, store, and process data from at least the light sensor and compare the data with state information about the mammal's circadian state or well-being and compares the operational information and the state information, and, based on the comparison, can generate at least one output signal.

An object of the present disclosure is to provide a lighting system that enables collecting and processing input about present light conditions surrounding a mammal, and, in particular a human, for generating an output that will alter the light conditions surrounding the mammal thereby, providing a better lighting environment. The output thereby increases the well-being of or "energizing" the mammal and/or reduces the resources, such as electricity, needed to provide the required light. Light conditions are primarily understood as conditions such as luminosity and color temperature, uniformity, stability and smooth transitions.

An object of the present disclosure is to provide a lamp that produces light that regulates the circadian rhythm at least partially according to a 24-hour cycle. A further object is to provide a lamp that can contribute to the regulation of the hormone melatonin from the pineal gland.

A further object is to provide a lamp that produces light that will regulate the pupil size. An object of the present device, system and method is to provide a lamp that interacts with and/or to responds to a system that collects and processes input about present light conditions surrounding a mammal and in particular a human, thereby providing a better lighting environment and thereby increasing the well-being or "energizing" the mammal and/or reducing the resources, such as electricity, needed to provide the required light. Another object is a lighting system that is intelligent and/or learning and enabled to regulate light based on a user's previous behavior.

Objects of the disclosure include optimizing the visual conditions of the user, increasing the quality of the lighting in the area surrounding the user, improving the physical working environment, stabilizing the user's biological rhythms, such as the circadian rhythm, increasing the general well-being of the user, an reducing the energy consumption required to maintain adequate or optimized lighting, thereby reducing the emission of greenhouse gasses (such as CO2) or particulate matter.

It is a primary object of the present disclosure to provide lighting conditions having a positive influence on the mental state of a person.

Accordingly, the above goals are achieved by a lighting system to be disclosed, a lamp or a light source to be disclosed and/or a combination of a lighting system and a lamp or a light to be disclosed.

In particular, an object of the disclosure is fulfilled by a lighting system for initiating change of a mammal's circadian state or well-being state, comprising:

at least one computational unit with a memory, a processor, at least one input and at least one output; and at least one light sensor with spectral and luminosity sensitivity and configured to provide information through a connection to said least one input of the at least one computational unit, the at least one computational unit configured to collect, store, and process data from the at least one light sensor generating operational information, to compare said operational information with information about the mammal's circadian state or well-being, and to generate at least one output signal on at least one connector for communicating with and controlling at least one light source;

wherein the computational unit is configured to calculate at least one output signal configured to output the setting of at least one light source or lamp to a color temperature range between 2700° K-7000° K; an intensity range between 10 to 1000 lumens; and a Ra-index greater than 92 at all values of color temperature and intensity.

Another object of the disclosure is fulfilled according to a lamp emitting light, comprising:

a housing configured to hold a reflector configured to reflect and/or direct light from at least one light source through a diffuser;

wherein said lamp further comprises a light control unit with at least one connector for communicating with and receiving regulating information from a lighting system as disclosed herein and configured to vary at least one light source so the light emitted from the lamp has a color temperature range between 2700° K-7000° K; an intensity range between 10 to 1000 lumens; and a Ra-index greater than 92 at all values of color temperature and intensity.

In particular an object of the disclosure is fulfilled by a system of a lighting system and a lamp or a light source as disclosed in herein. In the following section, separate units, elements or sub-systems will be disclosed.

One aspect of the disclosure is a lighting system for initiating change of a mammal's circadian state or well-being state, comprising:

at least one computational unit with a memory, a processor, at least one input and at least one output; and at least one light sensor with spectral and luminosity sensitivity configured to provide information through a connection to said least one input of the computational unit;

wherein the computational unit is configured to collect, store, and process data from the at least one light sensor generating operational information, and compare said operational information with information about the mammal's circadian state or well-being and to generate at least one output signal.

The lighting system thereby provides a system that affects the circadian rhythm or the well-being of the mammal, which can be a human and may be described as a personal user.

By dynamically and adaptively regulating the light surrounding the user, the lighting system will optimize the visual conditions of the user, optimize or better the quality of the lighting at a working location, change or stabilize the user's biological day rhythms, increase the overall well-being of the user and the user's overall health, reduce the energy consumption needed to provide the required light, and thereby reduce the emission of gasses such as CO2.

According to an embodiment of the disclosure, the light sensor is a point or a spot sensor measuring a limited area of a few $mm^2$ or $cm^2$.

According to an embodiment of the disclosure, the light sensor measures the ambient light by measuring at least light passing through part of a sphere or a whole sphere, with the light sensor typically measuring a hemisphere.

According to an embodiment of the disclosure, the light sensor measures at least part of the frequency spectrum of visible light. Typically the light sensor is sensitive to a wavelength range between 400 nm and 1200 nm.

According to an embodiment of the disclosure, the light sensor measures the light intensity from parts of lx to thousands of lx or sub-ranges therein.

According to an embodiment of the disclosure, the light sensor has a chromatic sensor and a lumen sensor or the light sensor is an integrated chromatic and lumen sensor.

The connector between the light sensor and the computational unit is configured to transmit operational data or information from the light sensor to the computational unit. In one embodiment, the connector is a cable. In another embodiment, the connector is a wireless connection.

According to an embodiment of the disclosure, the light sensor is integrated within the computational unit or attached directly to the computational unit. In another embodiment, an optical wave guide guides light to the light sensor with or without a lens arrangement with varying view of angle.

According to an embodiment of the disclosure, the light sensor or the optical wave guide is attached to a holder. The holder can be a pair of glasses or other types of headgear.

In various embodiments of the disclosure, the computational unit is a micro-processor connected to a device configured to connect to the light sensor; a multipurpose microcomputer such as a laptop, a handheld computer, a PDA, or a PC; or a smart phone.

According to various embodiments of the disclosure, the computational unit has a display or is configured to attach to or communicate with a display, and the computational unit may have an I/O-device or be configured to attach to or communicate with an I/O-device.

According to an embodiment of the disclosure, the computational unit has a touchscreen for display and for retrieving input. According to an embodiment of the disclosure, the computational unit has a CPU, a memory and input/output ports for retrieving and sending raw data or information. It is understood by one of ordinary skill in the art, that the CPU is at least configured to compare at least one data input from operational information with at least one data input from the state information.

The operational information relates to information retrieved by the lighting system, while operating the lighting system. The operational information can be information about the background light including data about chromaticity and intensity obtained from the light sensor.

The operational information can vary in time. The computational unit can be configured to retrieve, store and process operational information that varies with time. The state information refers to data or information about the state of the mammal. The state can be an actual state or a desired state. The state information can be pre-stored and stationary data about the personal user. In one embodiment, the state information is stating whether the personal user is an A-type person or a B-type person.

In another embodiment, the state information is whether the personal user has been travelling from one time zone to another time zone, i.e. has in increased probability of experiencing jet-lag.

In yet another embodiment the state information is dynamic and measured continuously.

In yet another embodiment the state information is the level of melatonin of the personal user.

In yet another embodiment the state information is the conductivity of part of the mammal's skin.

In yet another embodiment the state information is a personal user-selected input based on predefined selectable options relating to the well-being of the personal user.

In still another embodiment the state information is provided by a slide bar, connected with the system, with a "very tired" indication at one end and a "very fresh" indication at the other end. Alternatively, or in addition, there can be another slide bar with a "wake me up" indication at one end and a "put me to sleep" indication at the other end. The personal user sets the slide bar, thereby providing state information to the lighting system.

According to one embodiment, the output signal is an electrical signal generated to drive an indicator with a label that shows "too little light" or "too much light" and provide an instruction to the user to move.

According to another embodiment, the output signal is a text pre-selected from a series of predefined text strings defining instructions and displayed on a display or a computer screen. The instructions can vary in scope and wording from "too much red light—seek bluer light", "too bright red light—turn down red light", etc.

According to yet another embodiment, the output signal is a stimulus suitable for rewarding or punishing the mammal. As such the output signal can activate a feeding device, said feeding device being able to deliver food, drugs, medicine, and stimuli, for example.

According to yet another embodiment, the lighting system further comprises at least one connector for communicating with and controlling at least one light source.

The lighting system via an output signal sent through the at least the one connector controls the at least one light source's intensity or chromaticity.

In one embodiment, the connector is a wire configured to transmit a control signal. In another embodiment, the connector is a wireless connection configured to communicate with light sources via at least one communications standard.

In one embodiment the lighting system is configured for providing an output signal that will simulate a natural wake-up light, the wake-up light gradually increasing in intensity and increasing in color temperature from red towards blue. In another embodiment the lighting system is configured to provide an output signal that will simulate a natural "go-to-sleep" light, the light gradually decreasing in intensity and decreasing in color temperature from blue towards red.

In yet another embodiment the lighting system is configured for providing an output signal defined as "energy light" with a color temperature that is blue (e.g., 6,500° K) and with an intensity of 500-1,000 lumen, for example.

According to an embodiment of the disclosure, the lighting system further comprises at least one light control unit with a connection to said output and with a connection to at least one light source capable of emitting light at a variable chromaticity and/or luminosity.

The lighting system is a system that can control and optimize lighting surrounding the individual user based on the needs and/or desires and the user's circumstances, such as during work and during leisure.

According to one embodiment, at least one light control unit is integrated with at least one light source. According to one embodiment, the light control is an integrated circuit of a microcomputer and the light source is a computer screen display. According to one embodiment of the disclosure, the light source consists of at least two light emitters with different chromatic emissions, so as to emit light with a chromaticity between at least the extreme of at least two light emitters.

According to one embodiment, a light source with three light emitters with tree chromatic emissions is used, thereby enabling a light source to cover an area of color temperatures. In one embodiment, one emitter is a red LED, another emitter is a blue LED, and the third emitter is a yellow LED.

In one embodiment, a multiplicity of emitters is placed in a pattern forming a light source controlled by one light control unit. In another embodiment, identical light emitters are used, but at least one emitter is covered by a colored layer or coating thereby resulting in a color shift. According to one embodiment, the light source has a diffuser for diffusing, mixing or blending light from at least one light emitter, thereby mixing light from different emitters to form a uniform and pleasant light source. The diffuser can be sand-blasted glass or plastic, for example. The diffuser can also be a semi-transparent glass or plastic.

According to one embodiment, the lighting system further comprises at least one user interface with a connection to the computational unit for making personal data available to the computational unit. Thereby the user will be able to enter information required for the computational unit to process state information and operational information. In one embodiment, the user interface is a keyboard with alpha numeric keys. In another embodiment, the user interface is a touch-screen with either alpha numeric touch-areas or specifically designed touch-areas with pre-defined inputs, for example, sex, age, A-type person, and B-type person. In still other embodiments scroll bars, knops, buttons may be used as input devices to adjust color temperature, intensity, timing, and/or pre-stored light profiles that are constant in time or varying over time.

According to one embodiment, the lighting system further comprises at least one computational interface for connecting to at least one second computational unit configured to retrieve and store information. In this embodiment the lighting system may access and share information with remote databases or data-streaming devices holding information such as medical data about the user. The computational interface may be connected via a communications wire connected to a Universal Serial Bus or variants thereof, or a wireless connection such as Wi-Fi, Bluetooth, for example.

In some embodiments, the lighting system further comprises at least one biometric sensor unit with a connection to the computational unit for providing biometric data to the computational unit. The biometric sensor is configured to acquired state information used by the lighting unit. In one embodiment, the biometric sensor is a conductivity sensor in contact with the mammal's skin configured to gather information relating to the overall stress level or anxiety level, for example blood pressure. In another embodiment, the biometric sensor is configured to measure the user's pulse and thereby gather information about activity and over time variations or changes in the overall well-being of the user. In still another embodiment, the biometric sensor is configured to measure at least one level of a hormone or transmitter, melatonin for example. Melatonin levels are related to the circadian state of the user. The hormone or transmitter can be serotonin. Serotonin levels are related to the level of happiness of the user. The hormone or transmitter can be Cortisol. Cortisol levels are related to the level of stress of the user.

In some embodiments, the lighting system further comprises at least one activity sensor unit for providing activity data to the computational unit. The activity sensor provides state information relating to activities, for example, sleeping, walking, working, sitting, typing, resting and other types of user activities. The activity sensor provides operational information related to activities like movements in the environment and the light environment. The operational information can be the actual location of the lighting system and/or the user. In one embodiment, the activity sensor is an accelerometer configured to measure the acceleration of the user or the lighting system and provide information about the movement of the user or the lighting system. The information may be used to determining activities such as sleeping, resting, walking, running, working, or studying. In one embodiment, the activity sensor is a Global Positioning System (GPS) sensor configured to provide the latitude and longitude of a user. In one embodiment, the activity sensor is a GPS sensor configured to provide the user's position, thereby providing a basis for determining if the user is inside or outside or requesting the actual or forecasted weather conditions on the actual position of the user.

In some embodiments, the lighting system further comprises at least one additional sensor or detector unit. Among such additional sensors or detector units may be a time detector or unit, a location detector or unit, a work schedule detector or unit, a sleep pattern detector or unit, a daylight detector or unit, a mood detector or unit, a health detector or unit, a date detector or unit, an mammal energy detector or unit, and/or a connection detector or unit for receiving data or information from an unlisted unit via a protocol.

In one embodiment, the time detector or unit is a clock, which can be a digital clock embedded in the computational unit, an external clock or timer. In one embodiment, the location detector or unit is a GPS or a user interface for input of a location by the user. In one embodiment, the work schedule detector or unit is a calendar, which can be embedded in the computational unit or an external calendar or scheduler provided in a database stored on a different computer or entered. In one embodiment, the sleep pattern detector or unit is a device configured for measuring rapid eye movement (REM) signals and variations thereof, wherein the device is configured to interpret the signals. In one embodiment, the sleep pattern detector or unit is a handheld device with an accelerometer to be placed in contact with the user, wherein the contact can be direct or indirect, for example via a bed, to measure the movements of the user during sleep and further configured to categorize the movements according to the depth of the sleep. In one embodiment, the daylight detector or unit is a device configured to determine whether it is day or night. In one embodiment, the mood detector or unit is a unit that is configured to determine the user's mood (e.g., happy, depressed, or in-between) either by measuring a hormone level and comparing the level with a stored level, or by having a pre-defied mood-indicator to be selected by the user through an interface. In one embodiment, the health detector or unit is a storage unit with a medical record about the user compiled by a series of medical tests performed by a medical professional and stored on the storage unit that has a connection to the lighting system. In one embodiment, the date detector or unit is an electronic calendar. In one embodiment, the mammal energy detector or unit is a user interface configured to retrieve input regarding the mammal's energy levels. This can be done by having a list of pre-defined energy levels, or states, such as "feeling tired", "feeling sleepy", "feeling fresh", "feeling awake" and alike that can be selected by the user through an interface such as a touch-screen. In one embodiment, the connection detector or unit for receiving data or information from an unlisted unit via a protocol provides connection means or interface means with an open standard of communication protocols, or means that will broadcast its communication protocols when connected to the lighting unit. According to one embodiment of the device, system and method, the units or detectors are connected to the computational unit or said units or detectors are embedded in the computational unit.

The scope of the present disclosure includes variations of configurations of the disclosed sensors, detectors or units so that each sensor, detector or unit can be a separate device connected by wired or wireless connections or integrated.

According to one embodiment, the light control units or light sources are embedded in the computational unit.

The scope of the present disclosure includes variations of configurations of the disclosed control units, light sources, light emitters, or screens so that each of the control units, light sources, light emitters, or screens can be separate devices connected by wired or wireless connections or integrated.

The object of the present disclosure is met by a number of process features. In one aspect, a method for initiating change of a mammal's circadian state or well-being comprises:
    measuring the intensity and the chromaticity of light surrounding the mammal and providing the light data;
    collecting, storing, and processing measured light data and making operational information thereof; and
    generating an output signal for initiating change of the mammals surroundings.

The above discloses a process for altering or changing the circadian state or the well-being state of the mammal, which change results in an increased performance or output of the mammal.

The output signal is an audio-visual signal informing the mammal, for example, a human, to change the surrounding lights by leaving the present location. The output signal is based on operational information generated by the process. For example, an algorithm may include a summation of weighted light intensities at a given spectral value or range of spectral values as part of measured light data consisting of chromatic and intensity values.

In one embodiment, the method further comprises:
    retrieving or storing data about a mammals circadian state or well-being and making state information thereof; and
    comparing the operational information and the state information before generating an output based on the comparison.

The state information is provided by the user by entering information about the user's present state, for example being tired, fresh, awake, sleepy, or similar qualitative information through an input device.

In one embodiment of the method, the state information and/or operational information, along with the output, is stored and is continuously processed, or it is processed when prompted by the user to discover recurrent outputs that reflect the user's preferred outputs for given situations.

In a further embodiment of the method, the actual state information and/or operational information is compared with the stored or memorized state information and/or operational information, and. when the difference is slight, the preferred stored or memorized output is automatically suggested for approval by the personal user or automatically selected and activated.

In other embodiments of the intelligent lighting system, the comparison or the processing of the state information or the operational data is done by use of a neural network, fuzzy logic, or so-called intelligent computation to store and optimize or discover individual user patterns within a set of information.

In one embodiment, the state information is provided by the user by entering information about a desired state for example, to become tired, become fresh, wake-up, fall asleep, or other enter another absolute or relative state through an input, device.

In one embodiment the method further comprises varying at least one light source's luminosity or chromaticity, wherein at least one light source is present in the surroundings of the mammal generating an output signal for initiating a change of the mammals surrounding light conditions. The variation in light is a reduction of the intensity and a shift in the color temperature from bluish to reddish light emitting diodes in order to meet a user's desire to go to sleep. The variation in light is an increase of the intensity and a shift in the color temperature from reddish to bluish light emitting diodes in order to meet a user's desire to wake up. The variation in light is a constant high intensity, 1000 lumen, bluish, 6500° K light for a fixed period of 10 minutes, based on the user's desire to get a boost of energy to feel fresh and energized.

One of ordinary skill in the art will recognize that a mammal with pupils will perceive light intensity according to the size of the pupil. As such it is well known to the person skilled in the art to seek guidance in the literature for a particular mammal to determine the needed light intensity for a particular mammal and/or surroundings of the mammal.

One extreme example is a dark room with a mammal, such as an owl, with a good night vision and with spectral sensitivity, only requires a light source with a very low intensity, or a few lumen. Another example is a working area with incident natural light of some considerable intensity where the mammal is a human with pupils almost as small as possible and in a situation where the color temperature needs to be changed towards blue. In this case, a light source of one or more light bulbs totaling some 1000 W installed in a standard European grid with a blue filter will provide a sufficient blue light to match and sufficiently change the natural background light.

Likewise the person skilled in the art will recognize the usefulness of lenses or reflectors to focus or to concentrate light to the field of view of the mammal.

The term "chromaticity" is used to define the perceived color of the light. In general the chromaticity of the light is referred to and stated as the color temperature (CT), with a reference to the electromagnetic radiation emitted from a black body at a given temperature in degrees Kelvin, (° K). It is acknowledged that the original definition of color temperature is based on thermal radiation, and that many other light sources based on non-thermal radiation exist. Furthermore, a so-called corrected color temperature (CCT) is often used as the perceived, by a human, radiation from a black-body radiator.

One of ordinary skill in the art will recognize the presence of different standards and definitions, and the person skilled in the art has knowledge of conversions between and among different standards. If not, the person will readily be enabled by seeking literature explaining conversion amongst RGB-, LAB-, Hue-, CIE-etc. color spaces.

An object of the present disclosure is achieved by a lamp emitting light, comprising a housing configured to hold a reflector configured to reflect and/or direct light from a light source through a diffuser; wherein the lamp further comprises a light control unit with at least one connector for communicating with and receiving regulating information from a lighting system and configured to vary the light source so the light emitted from the lamp has a color temperature range between 2700° K-7000° K; an intensity range between 10 to 1000 lumens; and a Ra-index greater than 92 at all values of color temperature and intensity.

The input from a lighting system is at least a signal requesting a certain color temperature and an intensity.

The lamp is capable of producing a light that contributes to regulate the circadian state of a subject. The regulation is done in a simple and effective way by having a single source that can simulate the natural light's variation over a 24-hour cycle and essentially as it varies over a one year cycle. Furthermore, the quality is continuous variable to a high degree, and the lamp is energy efficient.

The reflector is a geometrically shaped object configured to reflect and direct light through the diffuser. The reflector may have a reflective coating that reflects the light.

In one embodiment, the reflector has a reflectance above 90% in the 400 nm-750 nm wavelength range. One coating that provides such reflectance is a barium sulphate-based coating. Other possible coatings include diffusive coatings such as GORE® Diffuse Reflector or equivalent reflectors. Besides a high and uniform reflectance, these diffusive coatings also mix light from different emitters.

The diffuser is generally a matted glass, plastic or equivalent semi-transparent material configured to mix light rays from different emitters to form a uniform directional light source.

Although the preferred embodiments include a reflector and a diffuser, one embodiment of the lamp uses only the reflector. In another embodiment, the lamp is without the reflector.

According to one embodiment, the light source comprises a plurality of light emitters, preferably light emitting diodes or LEDs, which make the lamp energy-efficient.

The lamp is therefore capable of producing a light that can vary and that is robust against failure of one or a few light emitters.

According to one embodiment, the light control unit is configured to detect the failure of at least one light emitter. Furthermore, the light control unit is configured to compensate for such detected failure of at least one light emitter, by tuning or regulating the remaining emitters.

According to one embodiment, the light emitters in the light source are configured on the basis color mixing of chromaticity binning using a plurality of bins, individually or a pre-selected plurality of bins formed to generate a warm white, neutral white, or cool white or combinations thereof.

The lamp utilizes a selected few light emitters in an efficient way because each light emitter contributes to a partition of the desired color-space.

The person skilled in the art is guided to a standard such as ANSI C78.377-2008, but the scope of this device, system and method is not limited to this particular standard, as the person skilled in the art may find an equivalent starting point in any other standard.

A partition, a part or a bin of a color space has a coordinate and a certain extent in the color space. One such color space is the CIE 1931 in which each position is determined by an x- and y-coordinate.

According to one embodiment, the light source comprises at least one red, at least one blue, at least one green, at least one royal blue, at least one cyan, at least one phosphor converted amber light emitters in combination with at least a white light emitter. The light source provides a color adjustable light source with tones of white. The person skilled in the art will understand, from the names of the colors, which wavelengths to start with.

According to one embodiment, the light source comprises at least one red, at least one green, and at least one blue light emitter, or comprises at least one white/yellow and phosphor converted light emitter in combination with at least one blue, and at least a first and a second red light emitter combination with at least a white light emitter. The light source provides an alternative color adjustable light source with tones of white.

According to one embodiment, the light source comprises at least one emitter having a DWL between 620-630 nm (red), at least one emitter having a DWL between 465-485 nm (blue), at least one emitter having a DWL between 520-535 nm (green), at least one emitter having a DWL between 450-465 nm (royal blue), at least one emitter having a DWL between 490-520 nm (cyan), at least one emitter having a DWL between 588-592 nm (amber) in combination with at least one emitting light source having a CCT between 2700° K-7000° K or at least one emitting warm white light emitting diode having a CCT between 2600° K-3700° K, at least one emitting neutral white light emitting diode having a CCT between 3700° K-5000° K, and at least one emitting cold white light emitting diode having a CCT between 5000° K-10,000° K. The light source provides a preferred and specific starting point for an intensity and color temperature variable light source. It is understood from the above that the mentioned wavelengths ranges are approximate and that the person skilled in the art will try to reduce the number of light sources used should it become possible. The wavelength ranges are approximate and define ranges for the mentioned colors.

According to one embodiment, the light source comprises at least one emitter having a DWL between 620-630 nm (red), at least one emitter having a DWL between 465-485 nm (blue), at least one emitter having a DWL between 520-535 nm (green) in combination with at least one emitting light source having a CCT between 2700° K-7000° K or at least one emitting warm white light emitting diode having a CCT between 2600° K-3700° K, at least one emitting neutral white light emitting diode having a CCT between 3700° K-5000° K, and at least one emitting cold white light emitting diode having a CCT between 5000° K-10,000° K.

According to one embodiment, the light control unit is configured to vary each light emitter by means of a lookup table, a programmed function, or an interpolation of said lookup table or programmed function, or both.

The lamp therefore has a light control unit that by means of any of the mentioned principles is capable of controlling or regulating each light emitter according to the bins or partitions of the color space and the location of the light emitters.

The system may be configured with a light control unit, which can be a small processor with a memory and an intelligent unit, to reflect the color space, the bins and the location of the light emitters in this color space, and by receiving an input from a lighting system, to make the lamp light with a particular intensity and color temperature lookup pre-stored settings of each light emitter in the light source and provide a control to each light emitters accordingly. In a similar manner, the light control unit can be configured with a mathematical formula with the same input and resulting in an output that will provide the required setting of each light emitter. In one embodiment interpolation is done between the tabulated values to obtain a smoother transition between desired points in color space and intensity.

According to one embodiment, the lamp further includes at least a second connector for communicating with and receiving regulating information via a standard wireless network with a standard protocol such as CAN, a private wireless lamp network for communicating with at least one other lamp, or a wired network with a standard protocol such as CAN. Further, the lamp may be configured to communicate with a lighting system or another lamp via a network.

According to one embodiment, the lighting system comprises:
at least one computational unit with a memory, a processor, at least one input and at least one output; and
at least one light sensor with spectral and luminosity sensitivity and that is configured to provide information through a connection to said least one input of the computational unit, which computational unit is configured to collect, store, and process data from at least the light sensor making operational information and comparing said operational information with state information about the mammal's circadian state or well-being state and which computational means compares the operational information and the state information for activating means for generating at least one output signal.

An object of the present disclosure is achieved by a kit of at least one lamp as disclosed and at least one lighting system as disclosed, where said lighting system further comprises at least one user interface with a connection to the computational unit configured to make personal data available for computation. Through the use of the interface, the user can select a pre-stored light sequence that varies in intensity and color.

According another embodiment, the lighting system further comprises at least one computational interface for connecting to at least one second computational unit for retrieving and storing information. Such a lighting system stores information about histories of usage and processes to make preferential light sequences that can be re-called and re-run.

An object of the present disclosure is achieved by a network of lamps comprising a plurality of lamps as disclosed and at least one lighting system as disclosed, wherein said lamps and least one lighting system are configured in zones, each zone being controlled or regulated by at least one lamp and at least one lighting system. Thereby an area with different working functions or more users with different requirements for light can easily be configured and obtained.

It is understood that the lamp as described can be implemented in a variety of forms ranging from small units, e.g., from pixel on a screen, that are close to be a small and simple light source, to larger unit used in, e.g., stadiums, halls or outdoor venues.

A person skilled in the art will understand or otherwise hereby be guided to understand a lamp broadly, and will sometimes find that the source more resembles a couple of light emitters than a table lamp and at other times more resembles an array of powerful spot lights.

As such, the disclosed examples of a network are only illustrative, and a person skilled in the art will be enabled to scale and transform the disclosure to other settings including office environments, halls, outdoor areas and arenas.

The primary object according to a first aspect of the present disclosure is achieved by a method for providing an output control parameter associated with a specific person for controlling a light output of a lamp adapted to vary said light output by said output control parameter, said light output being characterized by a color temperature, and said control parameter comprising a color temperature control parameter for controlling the color temperature of said light output, said method comprising:

providing a current time parameter representing the current local time of the day, providing a type parameter from a range of type parameters comprising at least a parameter representing a first person type and a parameter representing a second person type, providing a gender parameter from a range of gender parameters comprising a parameter representing a male person and a parameter representing a female person;

in a first alternative providing a first function being a multivariable function and comprising: a first variable representing the local time, a second variable representing said range of type parameters, and a third variable representing said range of gender parameters as input, a range of color temperature control parameters as output; said first function defining a first peak and a second peak of said range of color temperature control parameters with respect to said first variable, said first peak having a first maximum at a first time of the day and a first full width at half maximum of at least 30 minutes, said second peak having a second maximum at a second time of the day that is after said first time of the day and a second full width at half maximum of at least 30 minutes, said first function providing at a fixed value of said third variable an output representing a lower color temperature at said first time of the day for said first type of person than for said second type of person and an output representing a higher color temperature at said second time of the day for said first type of person than for said second type of person, and said first function further providing at a fixed value of said second variable an output representing a lower color temperature at said first time of the day and said second time of the day for a male person than for a female person;

in a second alternative providing a first function being a multivariable function representing:

$$T(t,x,y) = (T_0(t) - T_b) \cdot c_{type}(x) \cdot c_{gender}(y) + T_b,$$

where t is a first variable representing the local time, x is a second variable representing said range of type parameters, and y is a third variable representing said range of gender parameters, and said first, second, and third variables constitute an input for said first function, $T(t, x, y)$ is the output of said first function and covers a range of temperature control parameters, $T_0(t)$ is a first base function of the first variable t and defining a first peak and a second peak of said range of color temperature control, said first peak having a first maximum at a first time of the day and a first full width at half maximum of at least 30 minutes, said second peak having a second maximum at a second time of the day that is after said first time of the day and a second full width at half maximum of at least 30 minutes, $c_{type}(x)$ is a second base function of the second variable x and providing an output corresponding to a lower color temperature at said first time of the day for said first type of person than for said second type of person and an output representing a higher color temperature at said second time of the day for said first type of person than for said second type of person, $C_{gender}(y)$ is a third base function of the third variable y and providing an output corresponding to a lower color temperature at said first time of the day and said second time of the day for a male person than for a female person, and $T_b$ is a color temperature base level that is a positive constant for all values of said first, second, and third variables; and in both the first and the second alternatives, inputting into said first function said current time parameter as said first variable, said type parameter for said specific person as said second variable, and said gender parameter for said specific person as said third variable to yield said color temperature control parameter as the output from said first function.

Characterizing the light by a color temperature is to be understood a non-exclusive characterization, and the light simultaneously may be characterized alternatively or additionally in other ways, for example by an intensity, a spectrum, a polarization, or a radiance. Local time of the day is understood as encompassing time given as a Coordinated Universal Time (UTC) corrected for daylight saving time (summer/winter time) and the time zone in which the specific person is located. The first person type may correspond to a person of type A, i.e., an early riser as described elsewhere in this disclosure. The second person type may correspond to a person of type B, i.e., a late sleeper as described elsewhere in this disclosure.

The first function should be understood as encompassing any relation between the input and the permissible output. The first function should not be understood as limited to a single analytical expression. The first function being a multivariable function representing the analytical expression $T(t, x, y)$ should be understood as the first function encompassing all analytical expressions giving qualitative equivalent results as the explicitly defined $T(t, x, y)$, for example a rescaling by multiplying the right hand side by a constant gives a qualitative equivalent result. A full width at half maximum of at least a certain number of minutes should be understood as corresponding to an interval of time with a length of at least the certain number of minutes. By the control parameter being associated with a specific person is to be understand as the control parameter representing information on the specific person, for example type of person, gender, and age. The control parameter is understood as simultaneously representing a plurality of pieces of information, for example both the type of person and gender.

When the lamp is controlled by the output control parameter, the first function will give two "boosts" of blue light during the day that is adapted to be within the circadian stimulus range of most people, which will have the effect of an increased wellbeing for most persons. The specifying of the type of person and the gender further improves the effect.

In the first alternative, said first function may define a color temperature base level representing a positive constant color temperature over a first range of the local time, and said color temperature may be independent of said second variable and said third variable over said first range, and said first full width at half maximum may represent the width of said first peak at a color temperature corresponding to the mean of the color temperature of said first maximum and the color temperature at said color temperature base level, and said second full width at half maximum may represent the width of said second peak at a color temperature corresponding to the mean of the color temperature of said second maximum and the color temperature at said color temperature base level.

In the second alternative, said first base function $T_0(t)$ may be zero or approximately zero over a first range of the local time and said first full width at half maximum may represent the width of said first peak at the middle between said first maximum and $T_b$, and said second full width at half maximum may represent the width of said second peak at the middle between said second maximum and $T_b$.

In the first alternative, said first function may define a first depression between said first peak and said second peak at fixed values of said second and third variables, said first depression having a first minimum at a third time of the day and said first function may provide an output at said third time of the day that is the same or approximately the same for all values of said second variable and said third variable.

In the second alternative, said first base function $T_0(t)$ may define a first depression between said first peak and said second peak, said first depression having a first minimum at a third time of the day, said second base function $c_{type}(x)$ may provide an output at said third time of the day that is the same or approximately the same for all values of said second variable x, and said third base function $c_{type}(x)$ may provide an output at said third time of the day that is the same or approximately the same for all values of said third variable y.

Said first minimum and said color temperature base level may represent approximately the same color temperature, and/or said first range of the local time may comprise said third time of the day. Said first time of the day may be before noon according to the local time, and/or said second time of the day may be after noon according to the local time. Said first time of the day may be between 7 and 10 local time, and/or said second time may be between 12 and 15 local time.

Said first full width at half maximum may be longer than 2 hours, and/or said second full width at half maximum may be longer than 1 hour. Said first full width at half maximum may be less than 4 hours, and/or said second full width at half maximum may be less than 3 hours.

Said first range of the local time may have a length in the range 1 to 10 hours, 3 to 8 hours 5 to 6 hours, 15 to 30 minutes, 30 minutes to 1 hour, 1 to 2 hours, 2 to 3 hours, 3 to 4 hours, 4 to 5 hours, 5 to 6 hours, 6 to 7 hours, 7 to 8 hours, 9 to 10 hours, 10 to 11 hours, and/or 11 to 12 hours.

Said color temperature base level may correspond to the minimum color temperature control parameters of said output. Said color temperature base level may represent a color temperature in the range 2300°-3700° Kelvin, or in the range 2900° K-3100° K. Said first function may represent a color temperature between 5500° K and 6000° K for said second type of person and a female person at said first maximum. Said first function may represent a color temperature between 4500° K and 5000° K for said first type of person and a male person at said first maximum. Said first function may represent a color temperature between 5500° K and 6000° K for said first type of person and a female person at said second maximum. Said first function may represent a color temperature between 4500° K and 5000° K for said second type of person and a male person at said second maximum.

Said light output may further be characterized by an intensity and said control parameter may further comprise an intensity control parameter for controlling the intensity of said light output, and said method may further comprise: in the first alternative providing a second function comprising: a fourth variable representing the local time, a range of intensity control parameters as output, said second function defining a third peak and a fourth peak of said range of intensity control parameters, said third peak having a third maximum at a fourth time of day and a third full width at half maximum of at least 30 minutes, and said fourth peak having a fourth maximum at a fifth time of the day that is after said fourth time of the day and a fourth full width at half maximum of at least 30 minutes, or in the second alternative providing a second function representing:

$$I(t)=I_0(t)\cdot c,$$

where t is a fourth variable representing the local time and said fourth variable constitutes an input for said second function, I(t) is the output covering a range of intensity control parameters, $I_0(t)$ is a fourth base function of the fourth variable t and defining a third peak and a fourth peak of said range of color temperature control, said third peak having a third maximum at a fourth time of day and a third full width at half maximum of at least 30 minutes, said second peak having a fourth maximum at a fifth time of the day that is after said fourth time of the day and a fourth full width at half maximum of at least 30 minutes, and c is a correction factor, and in both the first and the second alternatives, inputting into said second function said current time parameter as said fourth variable to yield said intensity control parameter as the output from said second function.

The second function will improve the effect of "boosting" blue light during the day, which will increase wellbeing.

Said first variable and said fourth variable may be the same variable.

Said first peak and said third peak may have the same or approximately the same profile with respect to said first variable and/or said second peak, and said fourth peak may have the same or approximately the same profile with respect to said first variable.

In the first alternative, said second function may define an intensity base level representing a positive constant intensity over a second range of the local time, and said third full width at half maximum may represent the width of said third peak at an intensity corresponding to the mean of the intensity of said third maximum and the intensity at said intensity base level, and/or said fourth full width at half maximum may represent the width of said fourth peak at an intensity corresponding to the mean of the intensity of said fourth maximum and the intensity at said intensity base level.

In the second alternative, said fourth base $I_0(t)$ function may be constant or approximately constant over a second range of the local time and said third full width at half maximum may represent the width of said third peak at the middle between said third maximum and the minimum of said fourth base function $I_0(t)$, and/or said fourth full width at half maximum may represent the width of said fourth peak at the middle between said fourth maximum and the minimum of said fourth base function $I_0(t)$.

In the second alternative, said fourth base function $I_0(t)$ may be equal to or approximately equal to an intensity base level over a second range of the local time, where said intensity base level is a constant; said third full width at half maximum may represent the width of said third peak at the middle between said third maximum and said intensity base level, and/or said fourth full width at half maximum may be representing the width of said fourth peak at the middle between said fourth maximum and said intensity base level.

In the first alternative, said second function may define a second depression between said third peak and said fourth peak, said second depression having a second minimum at a sixth time of the day. In the second alternative, said fourth base function $I_0(t)$ may define a second depression between said third peak and said fourth peak, said second depression having a first minimum at a sixth time of the day.

Said second range of the local time may have a length in the range of 1 to 10 hours, 3 to 8 hours, 5 to 6 hours, 15 to 30 minutes, 30 minutes to 1 hour, 1 to 2 hours, 2 to 3 hours, 3 to 4 hours, 4 to 5 hours, 5 to 6 hours, 6 to 7 hours, 7 to 8 hours, 9 to 10 hours, 10 to 11 hours, 11 to 12 hours, 12 to 13 hours, and/or 13 to 14 hours.

Said first range of local time and said second range of the local time may be the same or approximately the same.

Said first time of the day and said fourth time of the day may be the same or approximately the same time of the day, and/or said second time of the day and said fifth time of the day may be the same or approximately the same time of the day, and/or said third time of the day and said sixth time of the day may be the same or approximately the same time of the day. This will further improve the effect of the "boosting" of blue light.

Said second minimum and said intensity base level may represent approximately the same intensity.

Said fourth time of the day may be before noon according to the local time, and/or said fifth time of the day may be after noon according to the local time. Said fourth time of the day may be between 7 and 10 local time, and/or said fifth time may be between 12 and 15 local time.

Said third full width at half maximum may be longer than 2 hours, and/or said fourth full width at half maximum may be longer than 1 hour. Said third full width at half maximum may be less than 4 hours, and/or said fourth full width at half maximum may be less than 3 hours.

The method may further comprise:
providing an age parameter from a range of age parameters representing different ages of a person, and in the first alternative said second function further being a multivariable function and further comprising: a fifth variable representing said range of age parameters as input, and said second function providing at a fixed value of said fourth variable an output that increases monotonically with said fifth variable, or in the second alternative said second function further being a multivariable function representing $$I(t,z)=I_0(t)\cdot c_{age}(z),$$

where t is said fourth variable representing the local time, and z is a fifth variable representing said range of age parameters, and said fourth and fifth variables constitute said input for said second function, $I(t, z)$ is the output of said second function and covers said range of intensity control parameters, $I_0(t)$ is said fourth base function of the fourth variable t and defining a third peak, and $c_{age}(z)$ is a fifth base function of said fifth variable z, said fifth base function constituting said correction factor c and providing an output representing an intensity that increases monotonically with the age of said person, and in both the first and the second alternatives said method further comprising: inputting into said second function said age parameter for said specific person as said fifth variable in addition to said current time parameter as said fourth variable to yield said intensity control parameter as the output from said second function.

With the above function of the fifth base function, the specifying of the age further improves the effect of the "boost" of blue light.

In the first alternative, said second function may provide at a fixed value of said fourth variable an output that increases exponentially with said fifth variable. In the second alternative, said fifth base function $c_{age}(z)$ may represent:

$$c_{age}(z)=1/(2^{(13/(z-25))}),$$

where the parameter z is given in the unit of years.

In the first alternative, said second function may be constant or approximately constant over a third range of the local time at a fixed value of said fifth variable, and said first function may define a fifth peak having a fifth maximum at a seventh time of day and a fifth full width at half maximum of at least 15 minutes, and said third range of the local time may be after said second and/or said fourth time of the day and may comprise said seventh time of the day. In the second alternative, said second base function may be constant or approximately constant over a third range of the local time, and said first base function may define a fifth peak having a fifth maximum at a seventh time of day and a fifth full width at half maximum of at least 15 minutes, and said third range of the local time may be after said second time of the day and may comprise said seventh time of the day. This will give a "boost" of blue light aimed at increasing the alertness of a person at the end of a working day.

Said seventh time of the day may be between 16 and 18 local time. Said fifth full width at half maximum may be longer than 30 minutes. Said fifth full width at half maximum may be less than 2 hours.

Said third range of the local time may have a length in the range of 30 minutes to 1 hour, 1 to 2 hours, 2 to 3 hours, or 3 to 4 hours.

Said first function may represent a color temperature between 4500° K and 5000° K for said first type of person and a female person at said fifth maximum. Said first function may represent a color temperature between 3750° K and 4250° K for said second type of person and a male person at said fifth maximum.

The primary object according to a second aspect of the present disclosure is achieved by a method for providing light for a specific person, said method comprising: providing a lamp adapted to vary its light output by an output control parameter, and providing said output control parameter by the method according to the first aspect of the present disclosure.

The primary object according to a third aspect of the present disclosure is achieved by a lighting system for providing an output control parameter associated with a specific person for controlling a light output of a lamp adapted to vary said light output by said output control parameter, said lighting system comprising: a computational unit adapted for performing an implementation of the method according to the first aspect of the present device, system, and method for providing said output control parameter, a time detector or unit connected to said computational unit for providing said local time of the day in said implementation, and a user interface connected to said computational unit for providing a type parameter from a range of type parameters comprising at least a parameter representing a first person type and a parameter representing a second person type in said implementation, and for providing a gender parameter from a range of gender parameters comprising a parameter representing a male person and a parameter representing a female person in said implementation.

Said user interface further may be configured for manually providing an age parameter from a range of age parameters representing different ages of a person in said implementation. The user interface may, for example, be a smart phone or a tablet computer with a touch screen and with the ability to communicate with the computational unit, for example via Bluetooth or wireless local area network.

The primary object according to a fourth aspect of the present disclosure is achieved by a kit comprising a lamp adapted to vary its light output by an output control parameter and lighting system according to the third aspect of the present disclosure for providing said output control parameter for controlling the light output of said lamp, said lighting system further being connected to said lamp for communicating said output control parameter to said lamp.

The first, second, third and fourth aspects of the present disclosure meeting the primary object of the present disclosure may comprise any one or more features disclosed in relation to any of the technologies for meeting any of the other objects of the present disclosure and to the aspects and embodiments related to these technologies. Further, any of the technologies for meeting any other object of the present disclosure and the aspects and embodiments related to these technologies may comprise any one or more features disclosed in relation to the first, second, third and fourth aspects of the present disclosure for meeting the primary object of the present disclosure.

DETAILED DESCRIPTION

Figure 20:
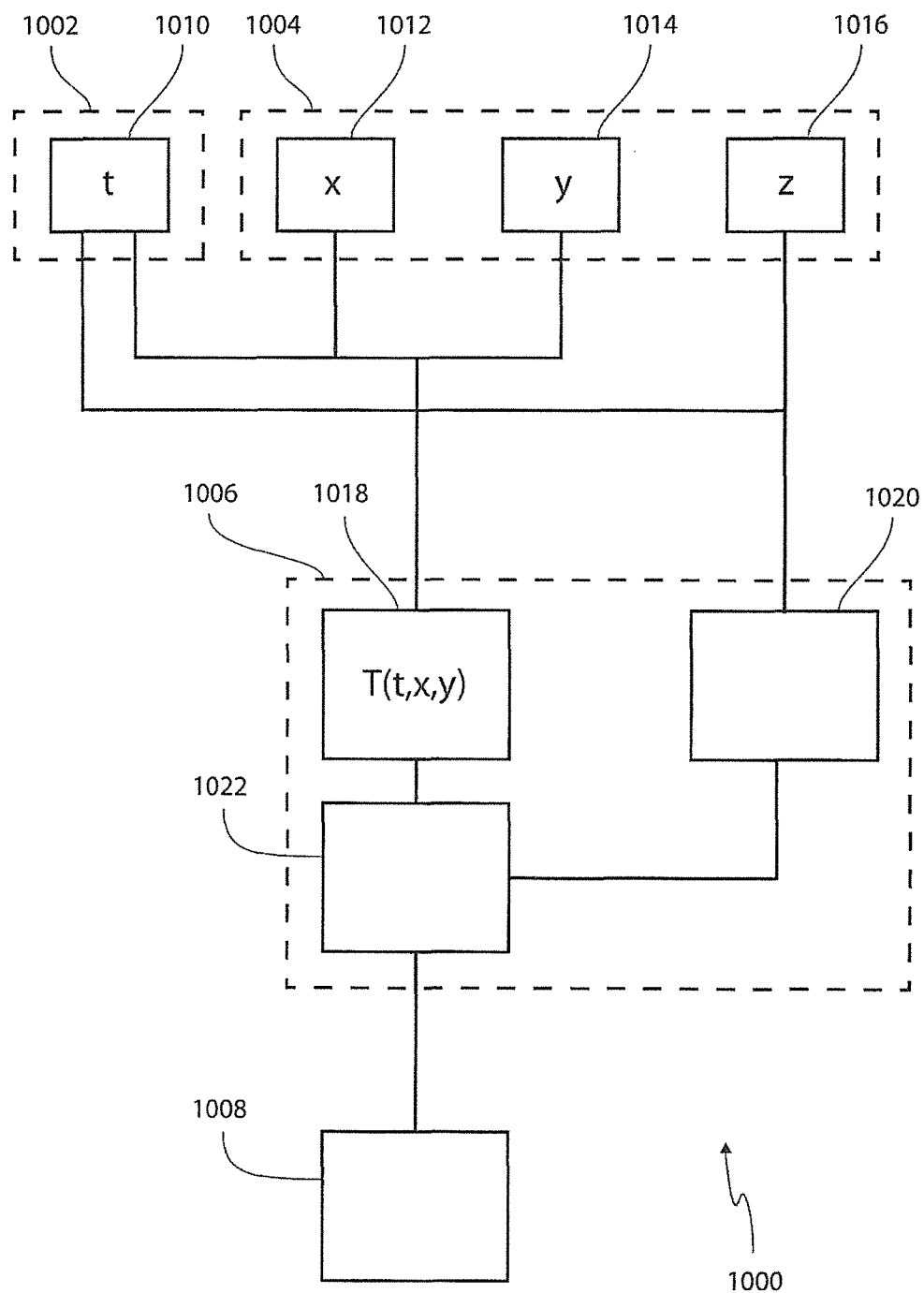
FIG. 20 shows a presently preferred embodiment of a lighting system according to the present disclosure.

FIG. 20 illustrates one embodiment of a lighting system 1000. The lighting system 1000 provides an output control parameter for controlling the light output of a lamp 1008 described elsewhere in this disclosure. The lighting system 1000 has a computational unit 1006 and a time detector or unit 1002 connected to the computational unit 1006. The time detector or unit 1002 provides the Coordinated Universal Time (UTC) corrected for daylight saving time (summer/winter time) and the time zone in which the lighting system is located as the current time 1010. The time detector or unit 1002 communicates the current time 1010 to the computational unit 1006.

The lighting system 1000 further has a user interface 1004 connected to the computational unit 1006. The user interface 1004 allows the specific user to manually specify if he or she is a person of type A or B (as described elsewhere in this disclosure), from which the user interface generates a type parameter 1012. The user interface 1004 than communicates the type parameter 1012 to the computational unit 1006.

The user interface 1004 further allows the specific user to manually specify his or her gender, from which the user interface generates a gender parameter 1014. The user interface 1004 then communicates the gender parameter 1014 to the computational unit 1006. The user interface 1004 further allows the specific user to manually specify his or her age, from which the user interface generates an age parameter 1016. The user interface 1004 then communicates the age parameter 1016 to the computational unit 1006.

The computational unit 1006, which for example can be a tablet computer or a smart phone, is configured to run an algorithm for providing an output control parameter 1022 based on the current time 1010, and type parameter 1012, the gender parameter 1014, and the age parameter 1016. Subsequently, the output control parameter 1022 is communicated to the lamp 1008, which subsequently adjusts its output according to the control parameter 1022.

The algorithm represents an implementation of a method for providing an output control parameter in the computational unit 1006. An analytical representation of the algorithm is given below with reference to FIGS. 21 to 23.

A first function 1018 that is a multivariable function is defined as:

$$T(t,x,y)=(T_0(t)-T_b) \cdot c_{type}(x) \cdot c_{gender}(y)+T_b,$$

in which t is a first variable corresponding to the current local time 1010, x is a second variable corresponding to said specified type parameter 1012, and y is a third variable corresponding to the specified gender parameter 1014. With this input, the first function T(t, x, y) gives a single output in the form of a color temperature control parameter. The color temperature control parameter constitutes a part of the output control parameter 1022 communicated to the lamp 1008, as is illustrated in FIG. 20.

Figure 21A:
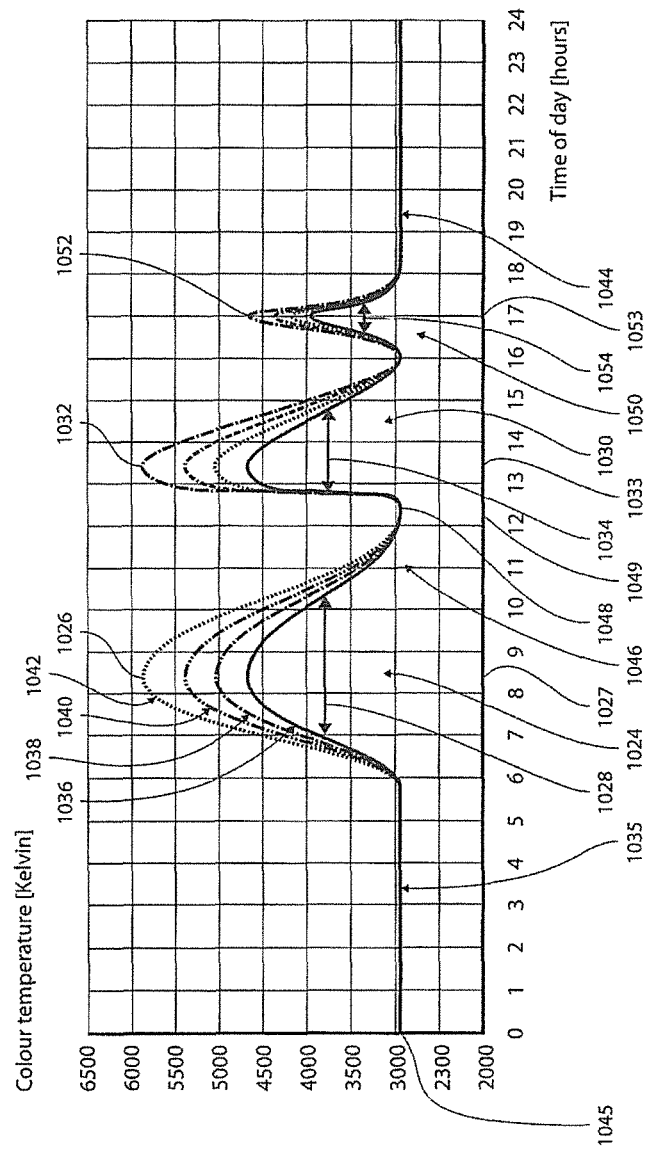
FIG. 21A shows a graph representing the first function according to a presently preferred embodiment of the disclosure.
Figure 21B:
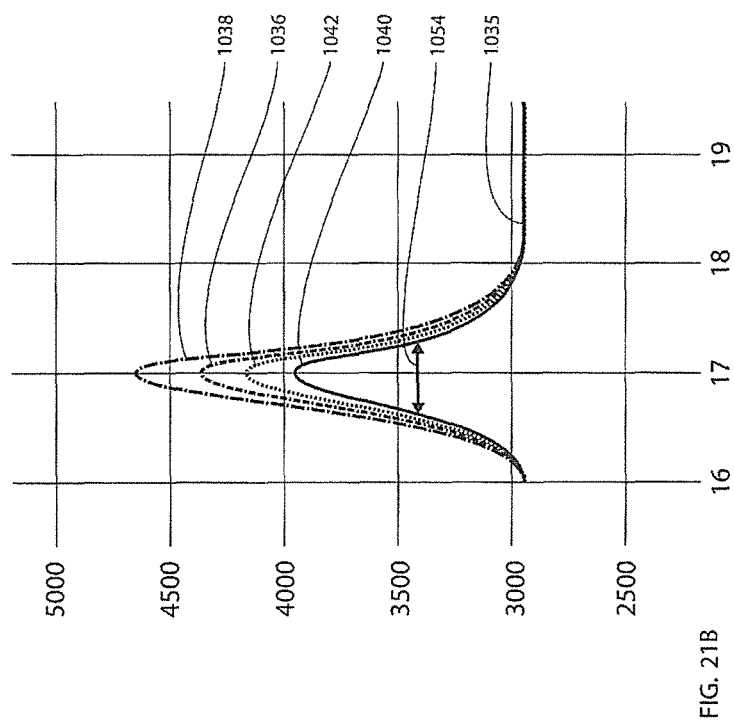
FIG. 21B is a blow-up of the graph shown in FIG. 21A.

$T_0(t)$ is a first base function 1035 of the first variable t, which is illustrated in FIGS. 21A-B. The first base function 1035 defines a first peak 1024, a second peak 1030, and a fifth peak 1050. The first peak 1024 has a first maximum 1026 at a first time of the day 1027 and has a first full width at half maximum 1028 that corresponds to a time interval of 3 hours and 15 minutes in length. The second peak 1030 has a second maximum 1032 at a second time of the day 1035 that is after said first time of the day and has a second full width at half maximum 1034 that corresponds to a time interval of 3 hours and 15 minutes in length. The fifth peak 1050 has a fifth maximum 1052 at a seventh time of the day 1053 that is after said first second of the day 1033 and has a fifth full width at half maximum 1054 that corresponds to a time interval of 45 minutes in length.

The first base function 1035 defines a first depression 1046 having a first minimum 1048 at a third time of the day 1049. The first depression 1046 is defined between the first peak 1024 and the second peak 1030.

$c_{type}(x)$ is a second base function of the second variable x. Before 12:30 local time $c_{type}(x)$ gives an output value of 1.0 if a type A person is specified and 1.4 if a type B person is specified. After 12:30 local time $c_{type}(x)$ gives an output value of 1.4 if a type A person is specified and 1.0 if a type B person is specified. $c_{gender}(y)$ is a third base function of the third variable y and gives an output value of 1.0 if the gender is specified as male and 1.2 if the gender is specified as female.

In FIGS. 21A-B, a male person of type A is represented by the curve indexed 1036, a female person of type A is represented by the curve indexed 1038, a male of type B is represented by the curve indexed 1040, a female of type B is represented by the curve indexed 1042. It should be noted that for the first peak 1024, the first base function 1035 and the curve 1036 representing a male person of type A are overlapping and that for the second peak 1030 and the fifth peak 1050, the first base function 1035 and the curve 1040 representing a male person of type B are overlapping.

$T_b$ is a constant with the value 2977° K representing a color temperature base level 1045. The first base function is zero for a first range of time 1044 covering a time interval 11 hours in long stretching from 19:00 in the evening to 06:00 in the morning. Consequently, the first function 1018 yields a color temperature control parameter that is equal to $T_b$ in the first range of time.

A second function 1020 that is a multivariable function is defined as:

$$I(t,z)=I_0(t) \cdot c_{age}(z),$$

in which t is a fourth variable corresponding to the current local time 1010 and, z is a second variable corresponding to the specified age parameter 1016. With this input, the second function I(t, z) gives a single output in the form of an intensity control parameter. The intensity control parameter constitutes a part of the output control parameter 1022 communicated to the lamp 1008, as is illustrated in FIG. 20.

Figure 22:
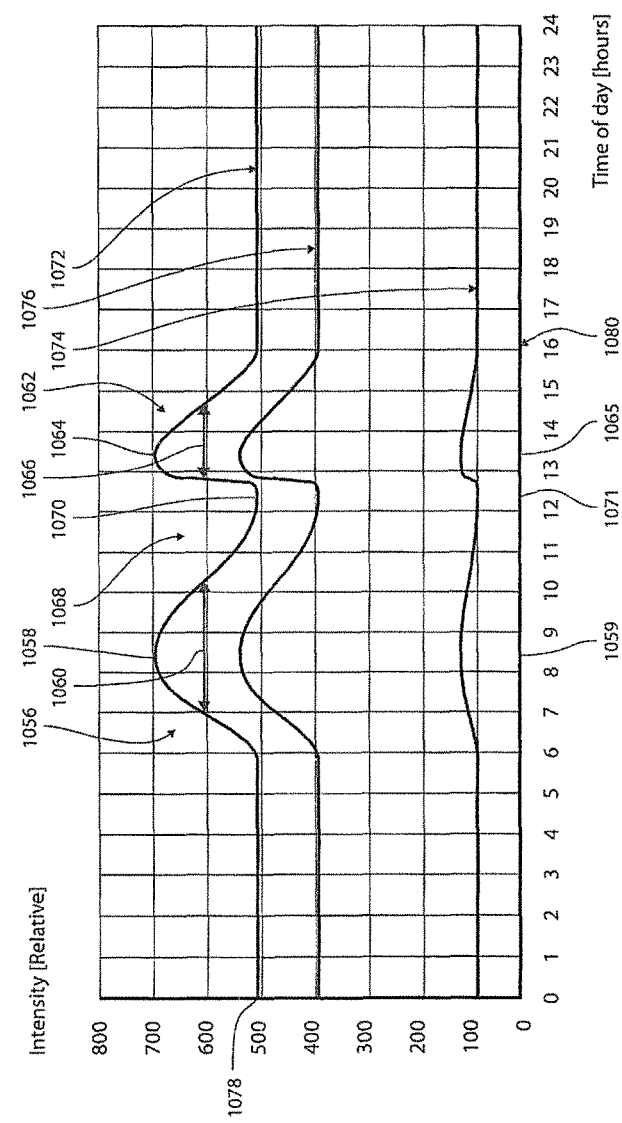
FIG. 22 shows a presently preferred embodiment of a second function according to the present disclosure.

$I_0(t)$ is a fourth base function 1072 of the first variable t, which is illustrated in FIG. 22. The fourth base function 1072 defines a third peak 1056 and a fourth peak 1062. The third peak 1056 has a third maximum 1058 at a fourth time of the day 1059 and has a third full width at half maximum 1060 that corresponds to a time interval of 3 hours and 15 minutes in length. The fourth peak 1062 has a fourth maximum 1064 at a fifth time of the day 1065 that is after said third time of the day and has a fourth full width at half maximum 1066 that corresponds to a time interval of 3 hours and 15 minutes in length.

The fourth base function 1072 defines a second depression 1068 having a second minimum 1070 at a sixth time of the day 1071. The second depression 1068 is defined between the third peak 1056 and the fourth peak 1062. The fourth base function 1072 is constant for a second range of time 1080 covering a time interval 14 hours in long stretching from 16:00 in the afternoon to 06:00 in the morning.

Figure 23:
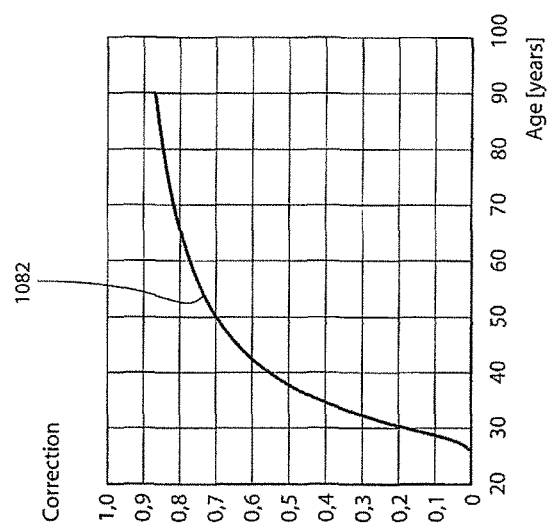
FIG. 23 shows a presently preferred embodiment of a fifth base function according to the present disclosure.

$c_{age}(z)$ is a fifth base function 1082, which is illustrated in FIG. 23 and is described by the analytical relation:

$$c_{age}(z)=1/(2^{\wedge}(13/(z-25))),$$

where the parameter z is given in the unit of years. The second function 1020 is illustrated in FIG. 22 and the curve indexed 1074 represents an age of 30 years and the curve indexed 1076 represents an age of 60 years.

The first peak 1024 and the second peak 1030 have the same profile as the third peak 1056 and the fourth peak 1062, respectively. The first time of the day 1027 and the fourth time of the day 1059 correspond to the same local time around 08:30. The second time of the day 1033 and the fifth time of the day 1065 correspond to the same local time around 13:30. The third time of the day 1049 and the sixth time of the day 1071 correspond to the same local time around 12:30. The above means that the color temperature and intensity are synchronized from 06:00 to 16:00. However, the fourth base function 1072 is constant for a third range of time 1080 covering a time interval of 2 hours in length stretching from 16:00 to 18:00 while the first function 1035 defines the fifth peak in this interval, which means that the color temperature and intensity are synchronized from 06:00 to 16:00.

Figure 1:
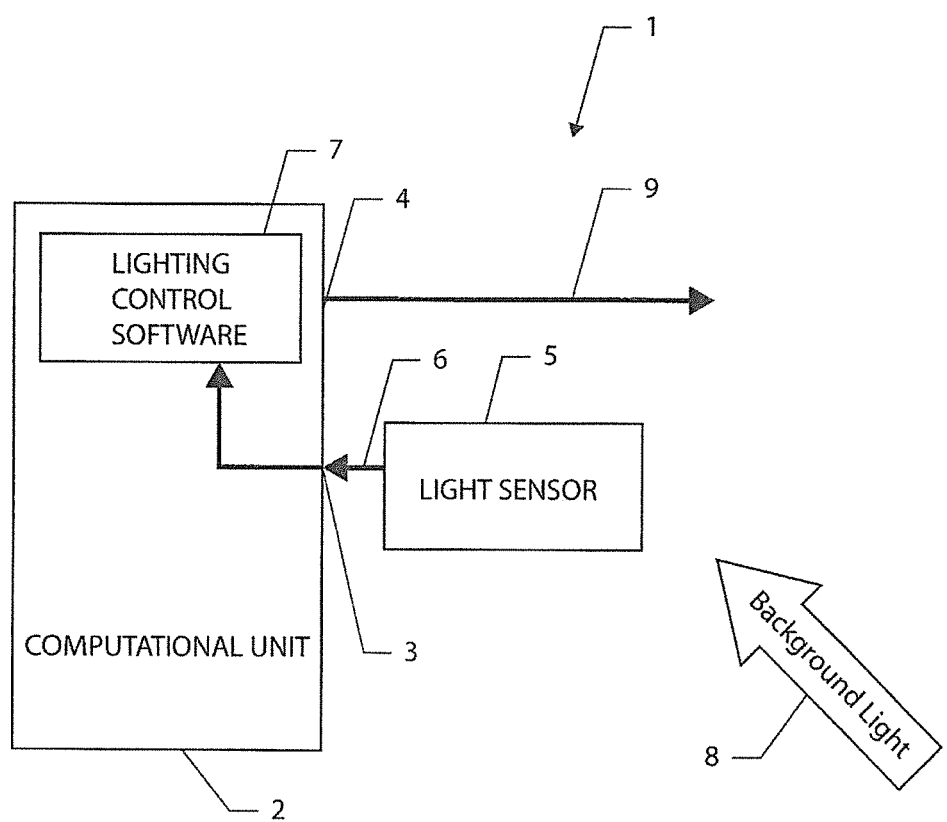
FIG. 1 shows an embodiment of a lighting system in accordance with the present disclosure, wherein the lighting system includes a computational unit with one input and one output.

FIG. 1 shows an embodiment of the system where a lighting system 1 with a computational unit 2 with one input 3 and one output 4 is shown. The input 3 is connected to a light sensor 5 through a connection 6, which in this embodiment is a wire. The light sensor 5 has means for measuring the intensity of the light and means for characterizing the chromaticity of the light.

The computational unit 2 has computational means 7 configured to provide a processing capability using light control software. The computational unit 2 includes at least a memory, a central processor and means for storing instructions for collecting, storing and processing data from the light sensor 5 and making information and for comparing the light information and comparing said light information with state information about a mammal's light and/or circadian state and which the computational means 7 compares the light information and the state information for activating means for generating at least one output signal 4.

The different information types will be described as follows:

The lighting system 1 and the light sensor 5 work in surroundings with background light 8.

In an extended version of the embodiment, the lighting system 1 has a connector 9 communicating with at least a light source to control luminance and/or color temperature.

Figure 2:
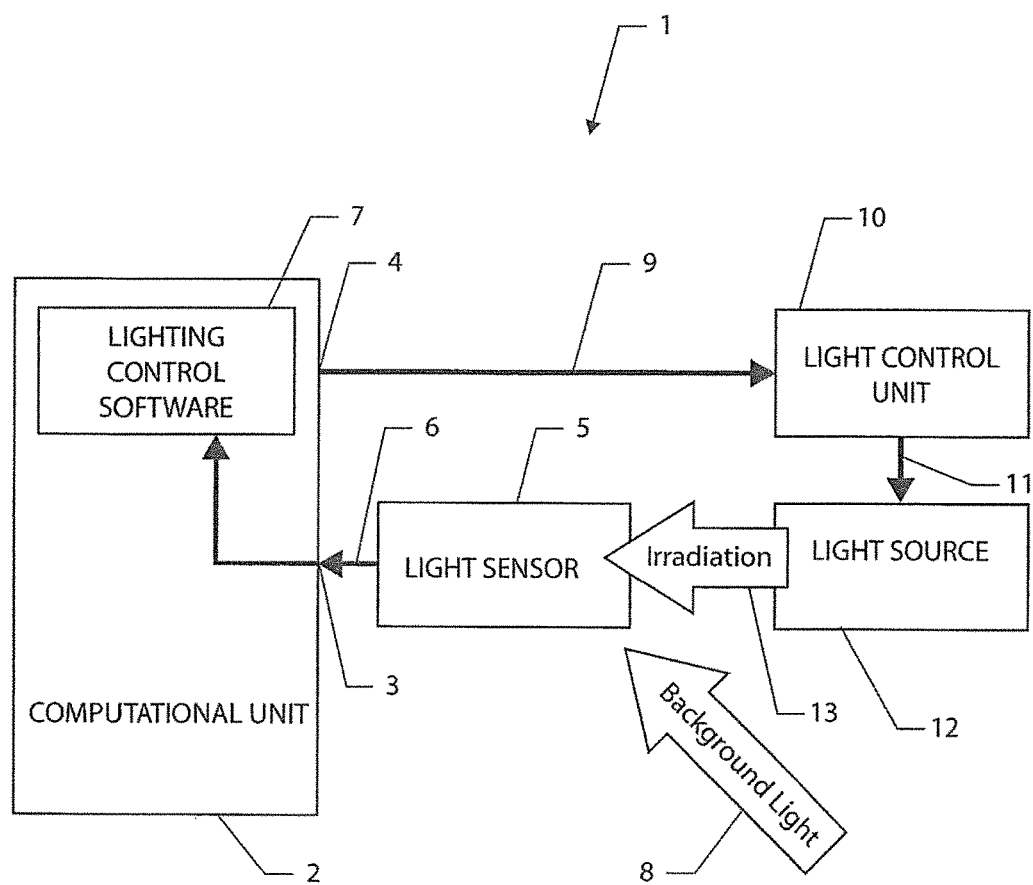
FIG. 2 shows an embodiment of the system of FIG. 1, further including a light source.

FIG. 2 shows an embodiment of the system where a lighting system 1 with a computational unit 2 and a light sensor 5 as seen in FIG. 1 are shown. This embodiment furthermore has the output 4 from the computational unit 2 communicating via a connection 9 to a light control unit 10 that has a connection 11 to a light source 12 that is capable of emitting light for irradiation 13 of a mammal mixed with the background light 8 to be collected or measured by the light sensor 5 connected to the input 3 of the computational unit 2.

Figure 3:
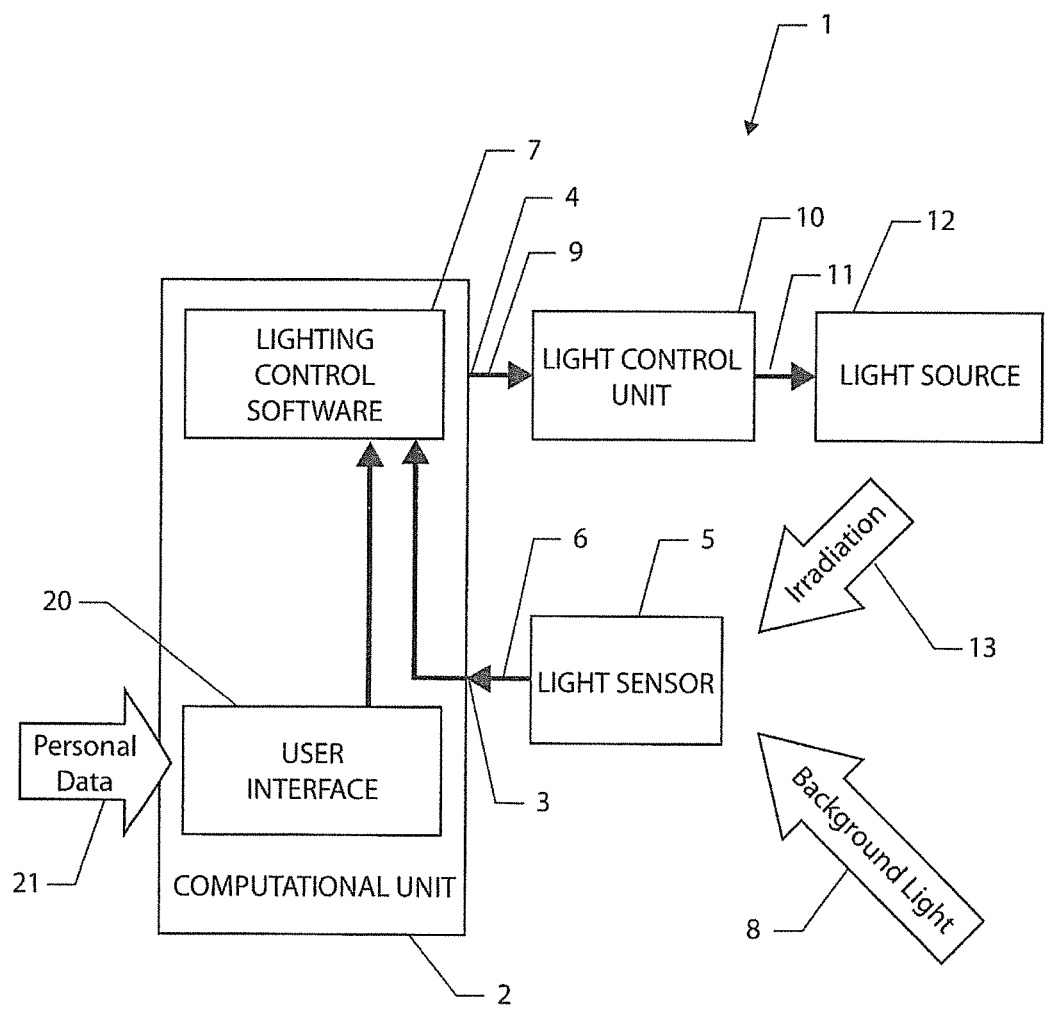
FIG. 3 shows an embodiment of the system of FIG. 1, further including a user interface for obtaining personal data.

FIG. 3 shows an embodiment of the system where a lighting system 1 with a computational unit 2, a light sensor 5, a light control unit 10 and a light source 12 as shown in FIGS. 1 and 2 are shown. This embodiment furthermore has a user interface 20 embedded in the computational unit 2, which user interface 20 is configured for receiving personal data 21. The computational unit 2 has a memory and processing and editing means for preparing the personal data 21 for adaptation and use by the computational means 7. Thereby personal data 21 such as information about a person's type (A-type or B-type), sex, age etc., can be processed and compared by the input 3 from the light sensor 5 by the computational means 3 for generating an output 4 that, via the light control unit 10, makes the light source 12 emit light with a luminance and chromaticity that is mixed with the background light 8 to alter the light conditions surrounding the person, thereby altering the circadian state of the person accordingly.

Figure 4:
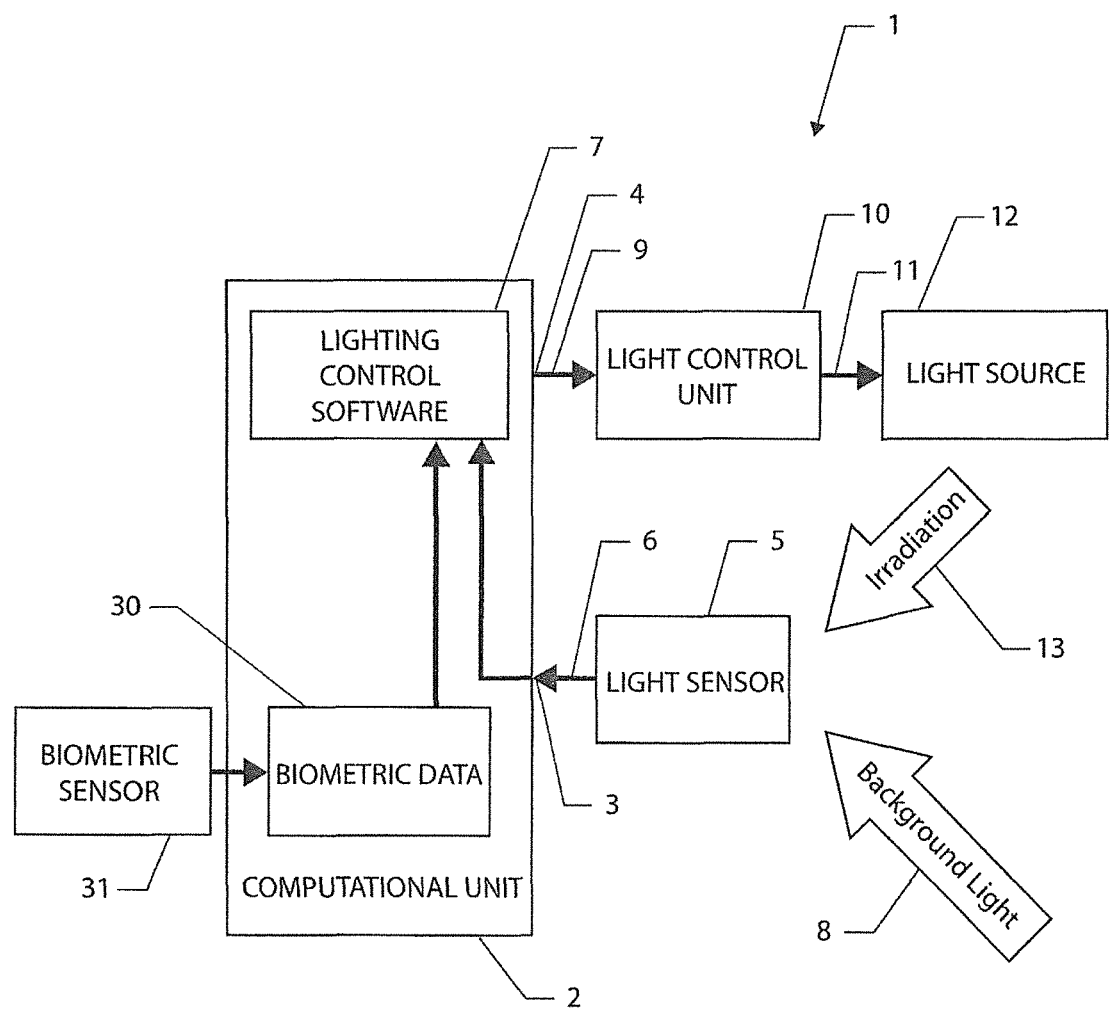
FIG. 4 shows an embodiment of the system of FIG. 1, further including a biometric sensor for receiving biometric data.

FIG. 4 shows an embodiment of the system where a lighting system 1 with a computational unit 2, a light sensor 5, a light control unit 10 and a light source 12 as shown in FIGS. 1, 2, and 3 are shown. In addition, this embodiment has a biometric sensor 31 connected the computational unit 2 for providing biometric data 30 that can be stored, processed and compared with input 3 from the light sensor 5 by the computational means 7. Thereby biometric data 30 can be used to generate an output 4 that, via the light control unit 10, makes the light source 12 emit light with a luminance and chromaticity that, when mixed with the background light 8, alters the light conditions surrounding the person, thereby altering the circadian state of the person accordingly. The biometric sensor 31 can have means for measuring the level of melatonin in a person or other physical data from which the person's circadian state can be derived. In an example of the shown embodiment, the computational unit 2 and the computational means 7 are loaded with instructions to accumulate (sum) the light intensity-weighted level of blue light (at around 430 nm) over a period of time no longer than a day, thereby to produce a "go" output if the accumulated resulting value is below a certain predefined threshold value and to produce a "stay" output if the accumulated resulting value is above the threshold value.

Figure 5:
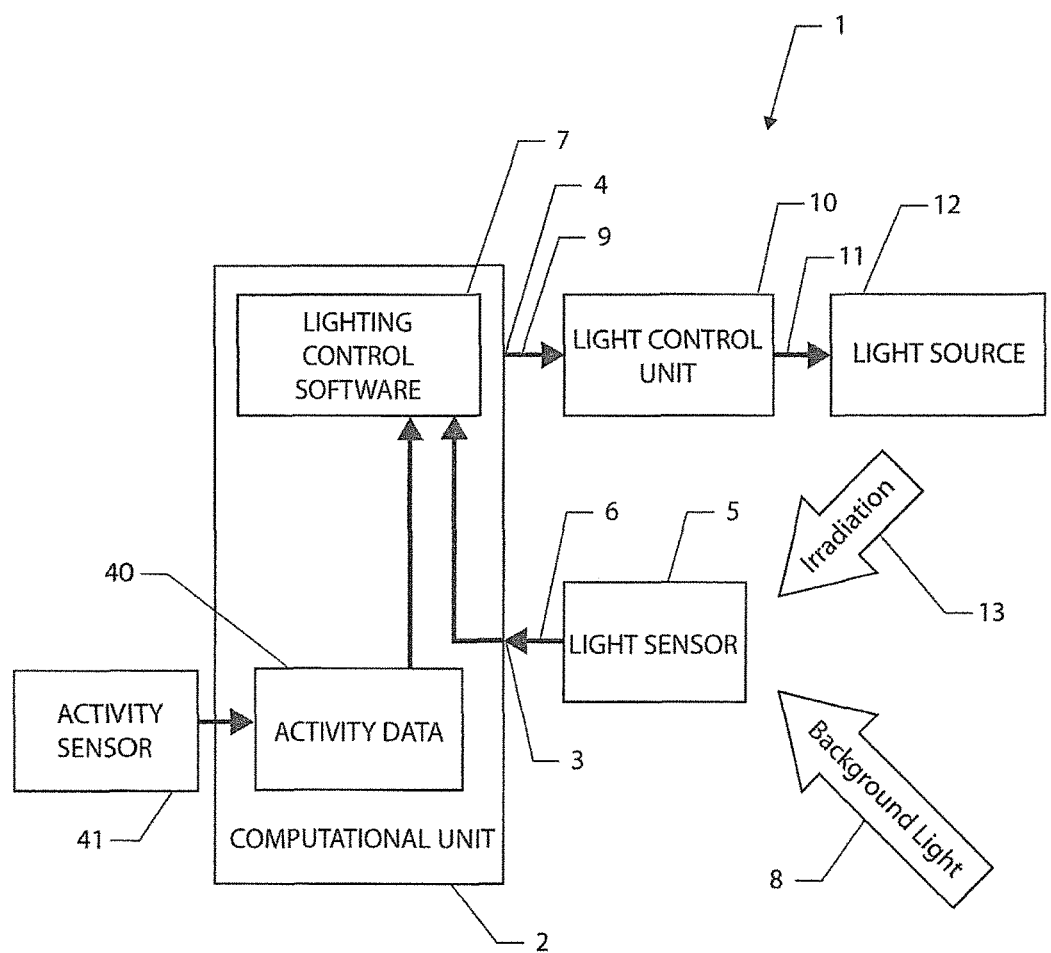
FIG. 5 shows an embodiment of the system of FIG. 1, further including an activity sensor for receiving activity data about the behavior of the personal user.

FIG. 5 shows an embodiment of the system where a lighting system 1 with a computational unit 2, a light sensor 5, a light control unit 10 and a light source 12 as shown in FIGS. 1, 2, 3, and 4 is shown. This embodiment furthermore has an activity sensor 41 connected to the computational unit 2 for providing activity data 40 that can be stored, processed, and compared with input 3 from the light sensor 5 by the computational means 7. Thereby activity data 40 can be used to generate an output 4 that, via the light control unit 10, makes the light source 12 emit light with a luminance and a chromaticity that, when mixed with the background light 8, alters the light conditions surrounding the person, thereby altering the circadian state of the person accordingly. The activity sensor 41 is configured to detect movements, such as with one or more accelerometers, of a person, and the activity sensor 41 may have pre-processing capabilities to determine if person is running, walking, sitting, working, typing, lying or sleeping, among other activities. In one embodiment, the activity sensor 41 is an accelerometer configured to work with processing system for determining a sleep-wake-cycle.

Figure 6:
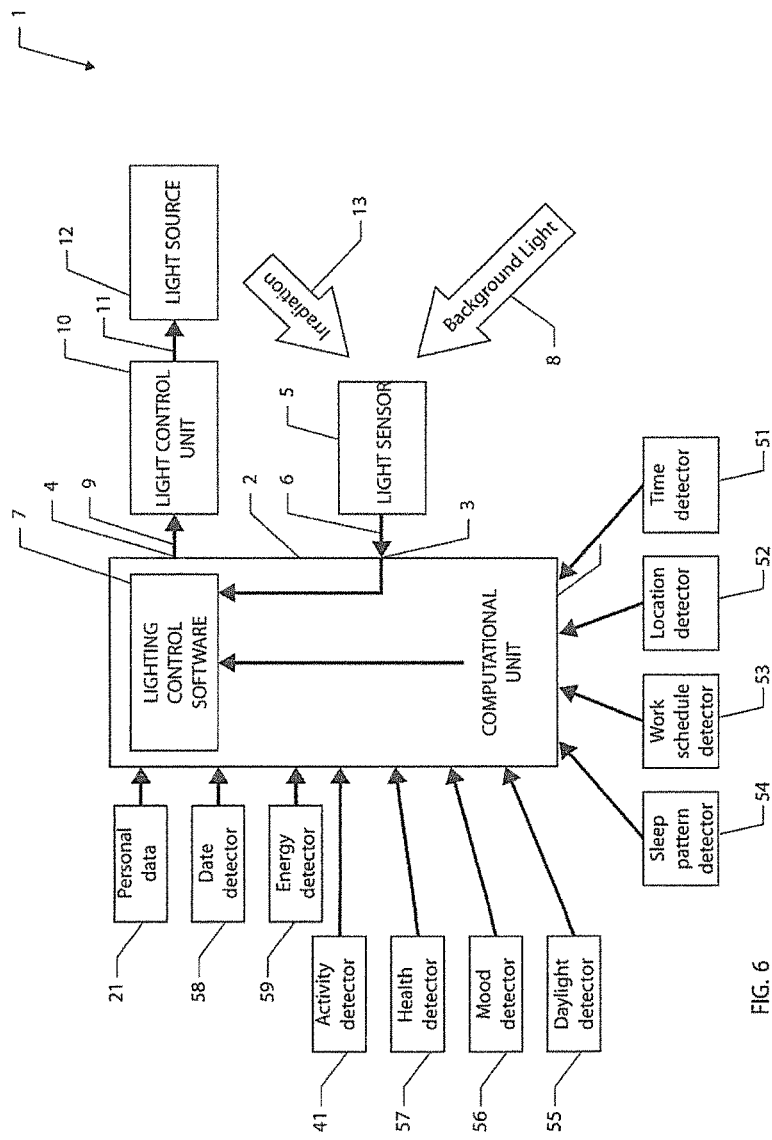
FIG. 6 shows an embodiment of the system of FIG. 1, further including a multiplicity of sensors or detectors for obtaining data and profiles for a combination of inputs to be processed for generating an output that will alter the background lights.

FIG. 6 shows an embodiment of the system where a lighting system 1 with a computational unit 2, a light sensor 5, a light control unit 10, and a light source 12 as shown in FIGS. 1, 2, 3, 4, and 5 is shown. In addition, this embodiment has a multiplicity of detectors or sensor units connected to the computational unit 2 for providing data that can be stored, processed, and compared with input 3 from the light sensor 5 by the computational means 7. The detectors or sensor units connected to the computational unit may include a time detector 51, which in this embodiment is a clock. Further included may be a location detector 52, which in this embodiment is a GPS sensor. Further included may be a work schedule detector 53, which in this embodiment is an electronic calendar. Further included may be a sleep pattern detector 54, which in this embodiment is an electrode for attachment to the mammal for detecting biometrical rhythms such as cardiac rhythms. Further included may be a daylight detector 55, which in this embodiment is a signal obtained from a local weather station or a national weather forecasting system. Further included may be a mood detector 56, which in this embodiment is a pad with a sensory element for measuring the conductivity of a surface area of the mammal. Further included may be a health detector 57, which in this embodiment is a connection and a protocol for receiving data from the mammals medical or physical record stored in a database. Further included may be a date detector 58, which in this embodiment is a connection and a protocol for receiving data from a calendar with information about the date and the solar position. Further included may be an energy detector 59, which in this embodiment is an interactive display with subjective levels of feelings of or perceived energy levels of the mammal to be entered.

Data from the detectors can be used to generate an output 4 that, via the light control unit 10, makes the light source 12 emit light with a luminance and a chromaticity that, when mixed with the background light 8, alters the light conditions surrounding the person thereby, altering the circadian state of the person accordingly.

Figure 7:
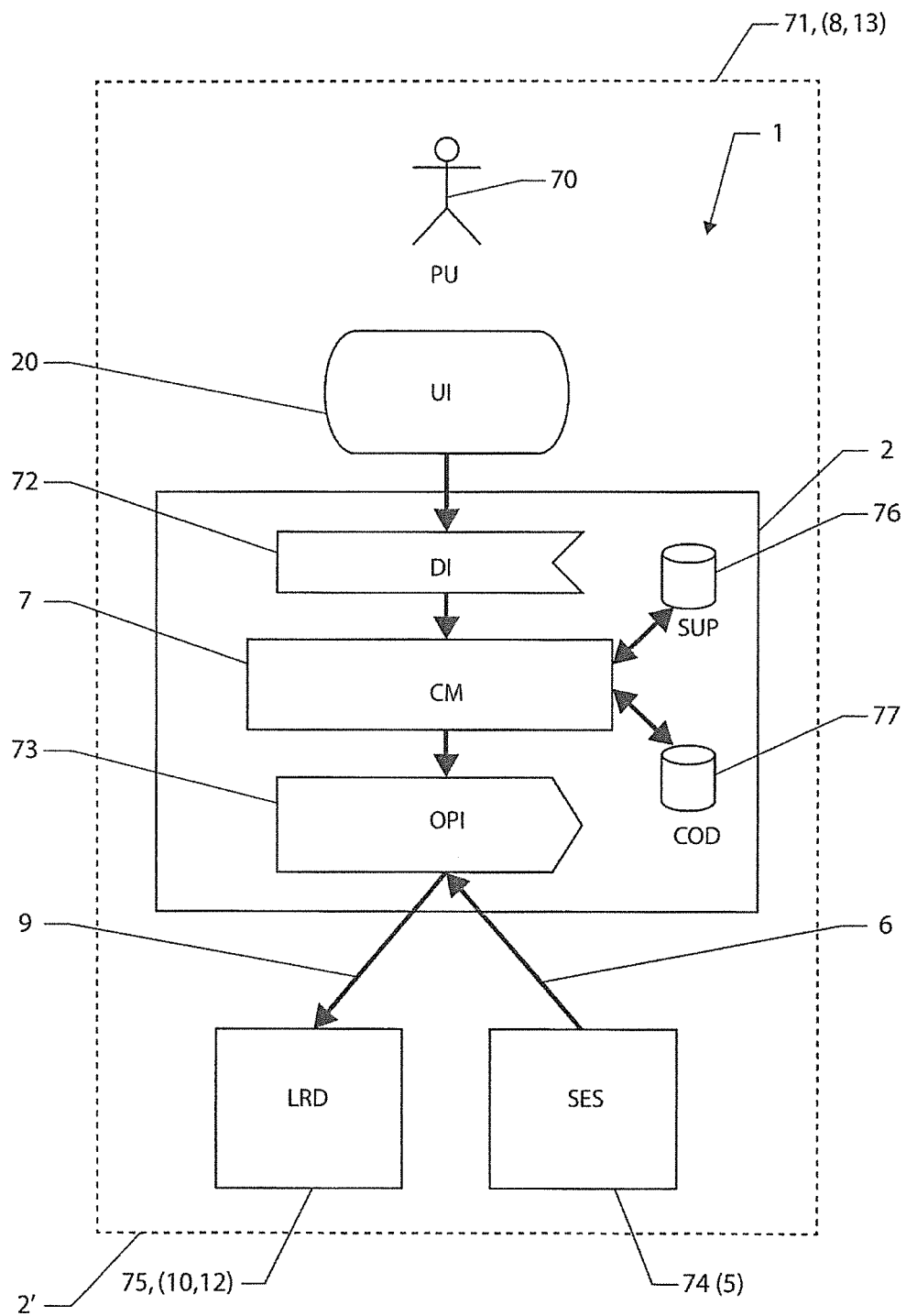
FIG. 7 shows an embodiment of a system diagram for data and information retrieval and output for an embodiment of the lighting system in accordance with this disclosure.

FIG. 7 shows an embodiment of a system diagram for data and information retrieval and output for an embodiment of the lighting system 1. The lighting system 1 works or operates in the vicinity of a mammal 70, represented here as a personal user (PU) 70, in a surrounding 71 that is illuminated by background light 8 and irradiation 13 from the lighting system 1. As such, the surrounding 71 is the vicinity of the personal user 70 and generally in the field of view of the personal user.

In this embodiment the lighting system has a user interface 20 that has a connection to a data interface (DI) 72 in the computational unit 2 that communicates with the computational means (CM) 7, which again communicates with an operational parameter interface (OPI) 73. The CM 7 is configured for communicating, storing and receiving data in at least one state user profile (SUP) 76 memory or structured memory forming a database. The CM 7 is further configured for communicating, storing, and receiving data and information in at least one collected operational database (COD) 77.

The OPI 73 is configured for receiving data from surrounding environment sensors (SES) 74, which in this embodiment is the light sensor 5, but in general may be one or more of a multiplicity of sensors or detectors, such as those shown and described previously and in FIG. 6.

The OPI 73 is further connected to a light radiating device (LRD) 75, which is an integrated unit consisting of a light source 12 and a light control unit 10. The LRD 75 is capable of lighting the surrounding 71 based on input from the PU 70. In one variant embodiment of the lighting system 1, the computational unit 2' has embedded the SES 74 and the LRD 75 as indicated in the Figure. Likewise the UI 20 could, in another variant of the embodiment, be integrated in one system, thereby having the lighting system 1 as one single unit.

Figure 8:
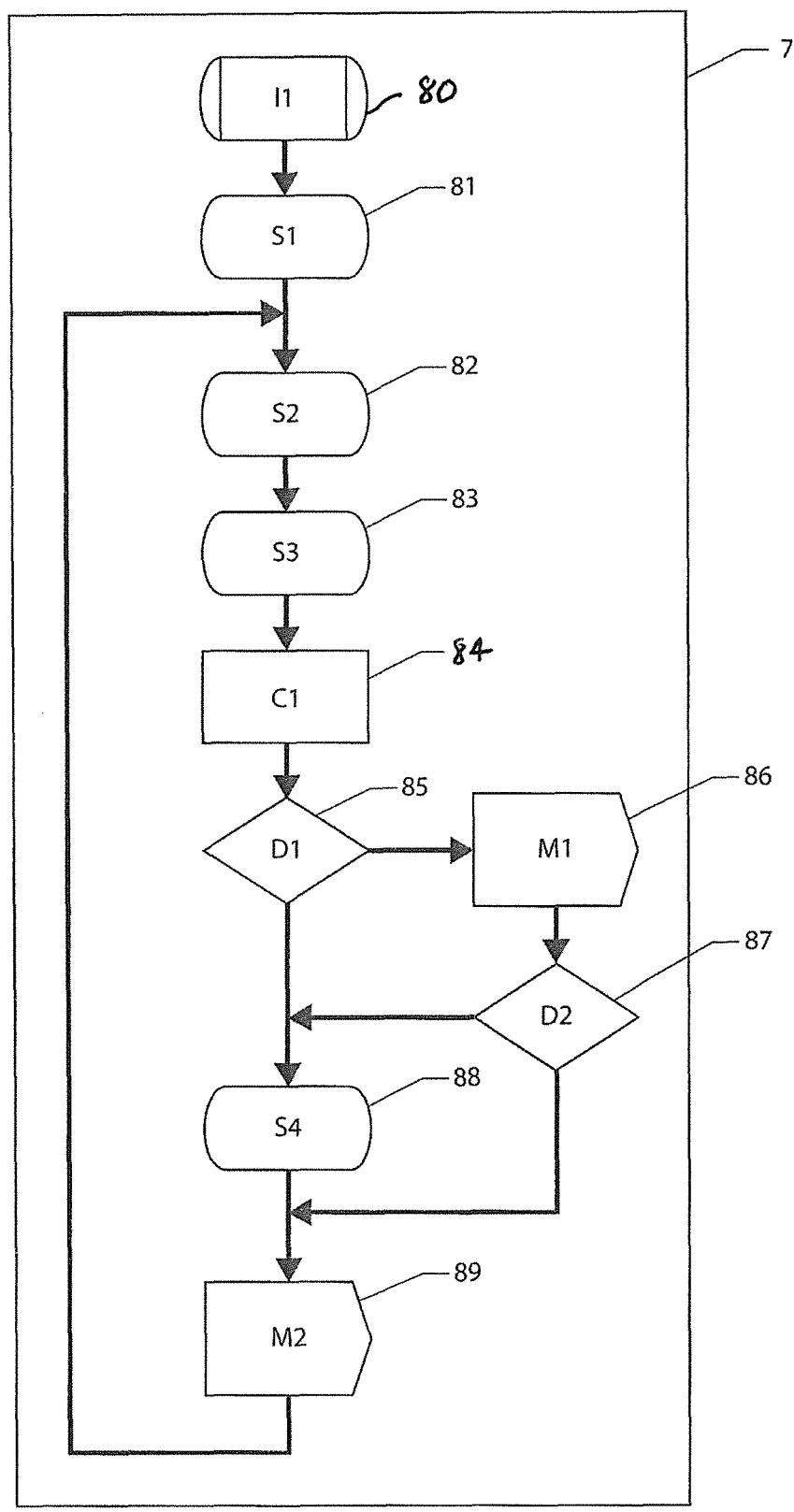
FIG. 8 shows a flow diagram of one embodiment of an algorithm that will coordinate the retrieval of data from the sensors, detectors and generate updated outputs to be used for control.

FIG. 8 shows a flow diagram of one embodiment of organized memory or sections of the computational means 7 for performing the steps and interactions of retrieving data and information from the sensors and detectors and generating appropriate outputs to be stored for usage by the output units. Performing an initialization (I1) 80 of the system is followed by performing a step that collects user profile data (S1) 81, such as age, sex, chronotype, etc.

The S1 81 is followed by performing a step that collects personal user preferences (S2) 82, such as PC-light, reading light, sealing light, etc.

The S2 82 is followed by performing a step that collects environment parameters (S3) 83, such as light conditions (e.g., background light 8, irradiated light 12 and combinations thereof), and time of the day, as well as data stored in databases or memories such as a storage S4 88 either in or outside the computational unit 2 or the computational means 7.

The steps of collecting data or information S1 S2, S3 81, 82, 83 are followed by a processing step, computation C1 84, that compute parameters based on data collected in S1, S2, S3, S4 81, 82, and 83.

The computation C1 84 is followed by a decision D1 step 85, that decides if the parameters calculated in C1 require personal user 70 acknowledgement. If personal user acknowledgement is required, then a manual M1 prompt 86 for personal acceptance is awaited and followed by a decision D2 87 whether the personal user did accept.

If no personal user acknowledgment is required, then the process goes to a step of storage S4 88, were the parameters are stored. If the personal user accepted in D2 87, then the storage S4 88 is adjusted accordingly. If the personal user acceptance in D2 87 is not accepted, then the process is taken to a step of performing an output M2 89 of operational parameters.

The process is then taken to a stage between S1 81 and S2 82 for an iterative loop process iterated from S2 82.

Figure 9:
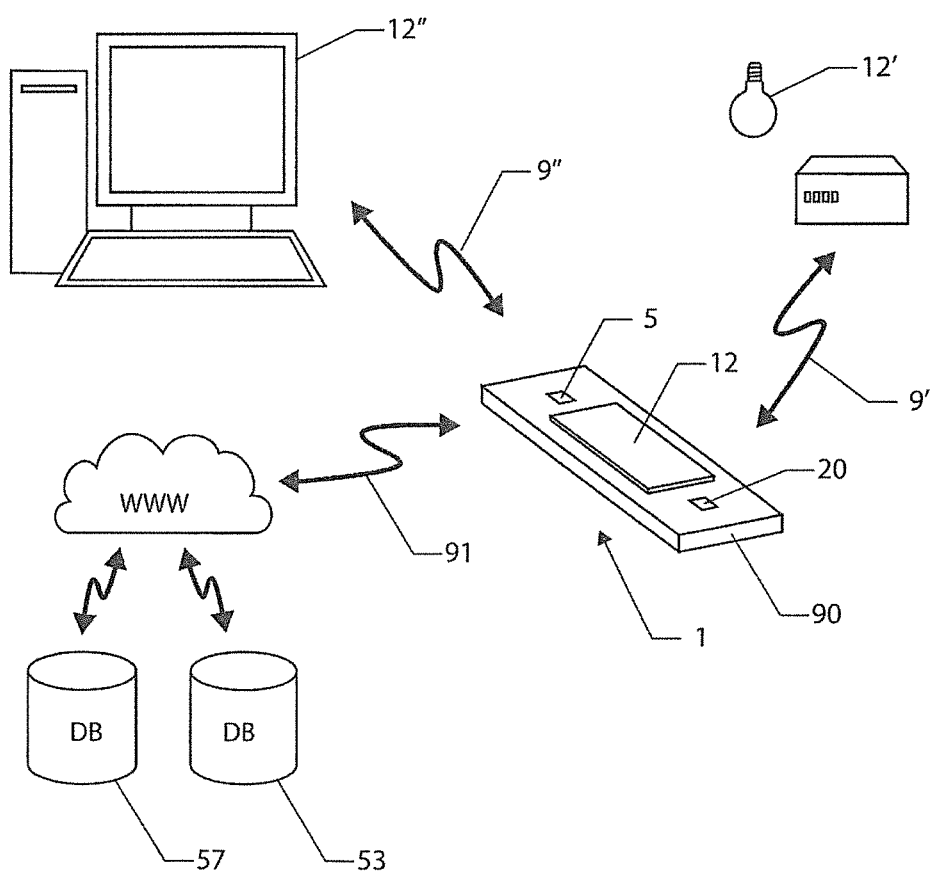
FIG. 9 shows an embodiment of a lighting system in accordance with this disclosure, wherein the lighting system includes at least a hand held device with a user interface and a light source and a light sensor.

FIG. 9 shows an embodiment of a lighting system 1 where the lighting system 1 includes at least a hand held device 90 with a user interface 20 and a light source 12 and a light sensor 5. In one embodiment the user interface 20 and the light source 12 are the same device such as a touch-screen.

The hand held device 90 has a computational unit 2 with computational means 7 embedded along with a wireless communication system for making wireless connections 9', 9" for units with external light sources 12', 12".

In this embodiment the hand held device 90 controls a light source 12' being a lamp, with Light Emitting Diodes (LED) as emitters placed for lighting a room. In this embodiment the hand held device 90 controls a light source 12" being a screen on a personal computer. The hand held device 90 further advantageously has a wireless internet connection 91 for communication with databases DB.

In this embodiment a first database DB 53 is provided with data about the personal user's work schedule for input to the computational unit 7 for processing. In this embodiment a second database DB 57 is provided with data about the personal user's health record with appropriate information.

Figure 10:
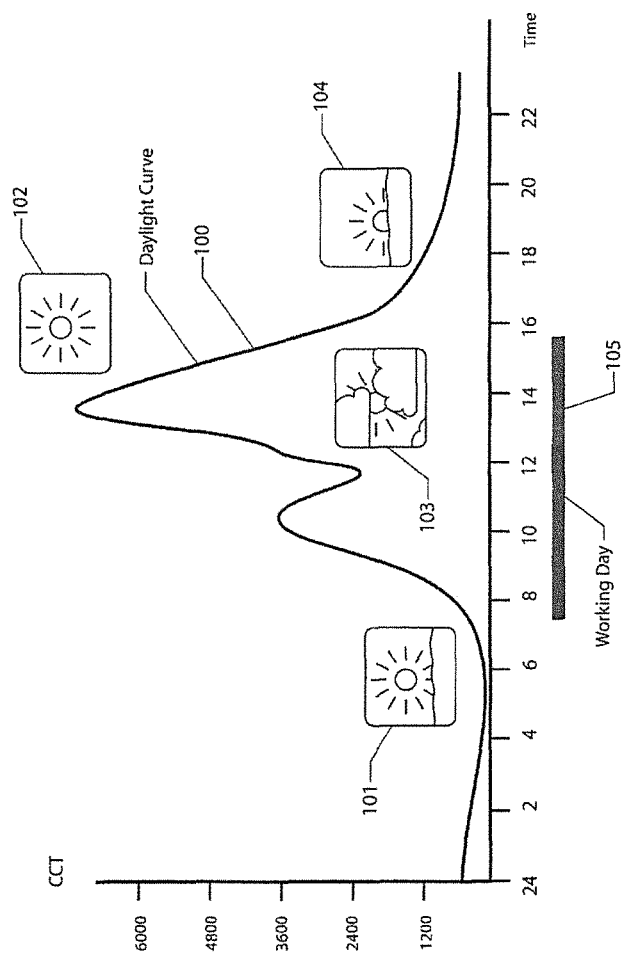
FIG. 10 shows an example of the corrected color temperature (CCT) during a day.

FIG. 10 shows a typical daylight curve 100 with the corrected color temperature (CCT) plotted against time. The daylight curve 100 illustrates variation during a 24-hour period with notable color temperatures at dawn 101, during clear sky day afternoon 102, on a cloudy day at noon 103, and at dusk 104. Also shown is a typical working day 105 starting at 8:00 finishing at 16:00. On a different day the daylight curve 100 naturally will emerge different caused by the location of the sun, the weather and the location.

The shown daylight curve will be used in the following example as basis or a reference light curve to which the described lighting system will be used to initiate a change of person's circadian state.

Figure 11:
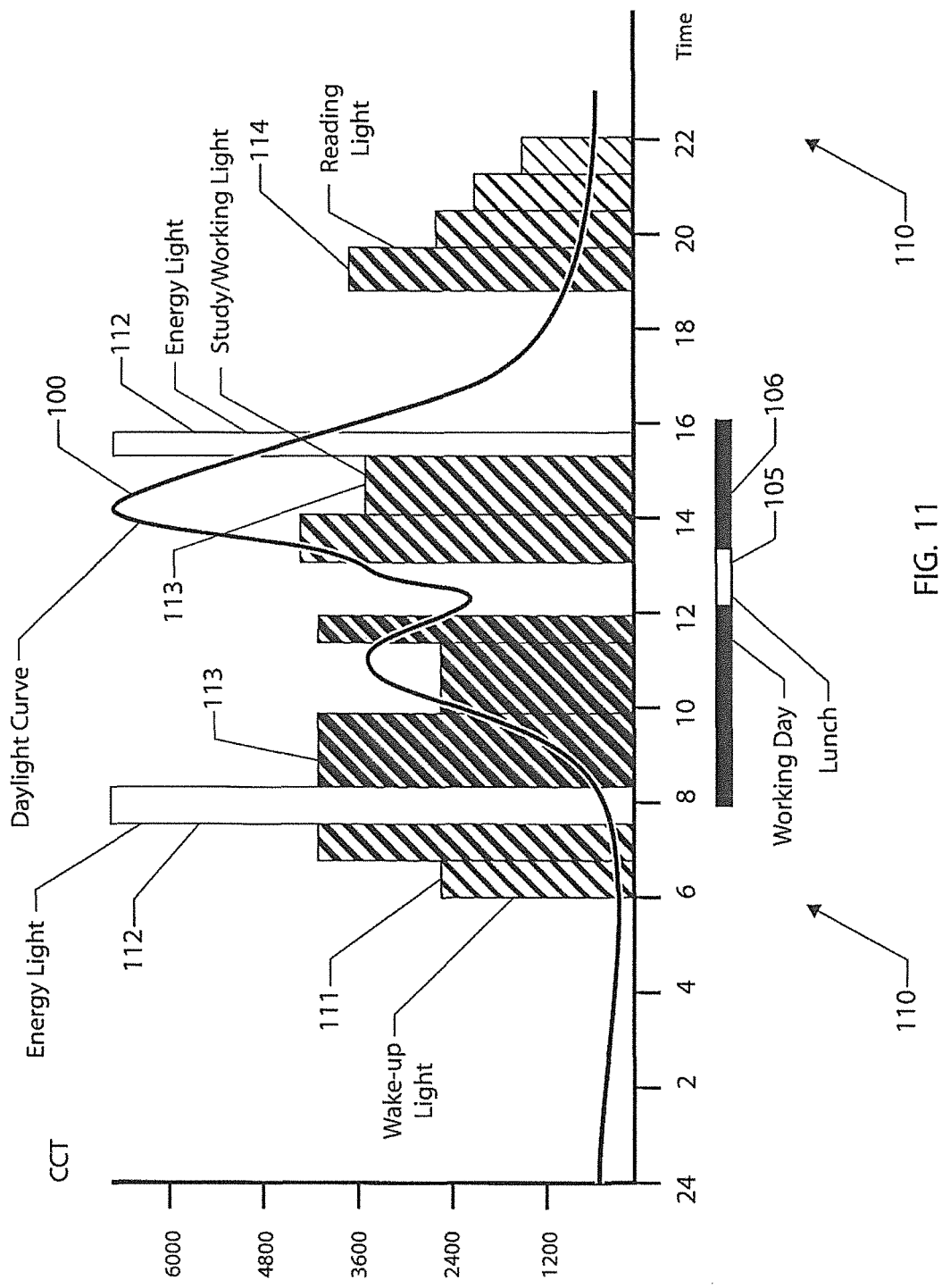
FIG. 11 shows an example of the outputs of a lighting system during a personal user's day, including a working day.

FIG. 11 shows the daylight curve 100 from FIG. 10 with a series of outputs from the light source during the day and as a result of the lighting system 1. The output is a series of lights 110 with varying luminosity and chromaticity according to the earlier description such that:

06:00-7:30: At dawn the lighting system gradually increases the color temperature of the light source during a period with wake-up light 111 to help the person to wake up. The wake-up light 111 comes from a light source being a lamp in the bedroom and is controlled by a wireless connection with the computational unit.

7:30-8:30: Just before work, a burst of energy-light 112, primarily blue or warm light at a CCT at about 6500° K, is emitted to boost the persons energy levels to become alert, effective and productive entering work.

8:30-12:00: During part of a working day 105, a variable study or working light 113 is emitted with a CCT varying between approximately 2400° K and 4500° K based on the measuring the CCT from the background light with the light sensor and calculating a compensating output via a light source to generate the study or working light 113 needed to compensate the background light for a desirable light or a fixed length preselected by the user.

12:00-13:00: During a lunch break 116, the lighting system is off.

13:00-15:00: During part of a working day 105, a variable study or working light 113 is emitted using the same principle as between 8:30-12:00.

15:00-15:30: At the end of the working day 105, a burst of energy-light 112 is emitted to energize the personal user before getting in the car for a drive, thereby minimizing the risk of fatigue that can or will result in an accident.

15:30-18:30: During afternoon and early evening the lighting system is simply off.

18:30-22:00: At the end of the day, indoor activities are performed and the lighting system provides a light, which CCT gradually decreases from about 4000° K to 1500° K to prepare the personal user to enter sleep.

Otherwise, that is during night, the lighting system is, in this example, idling.

Figure 12:
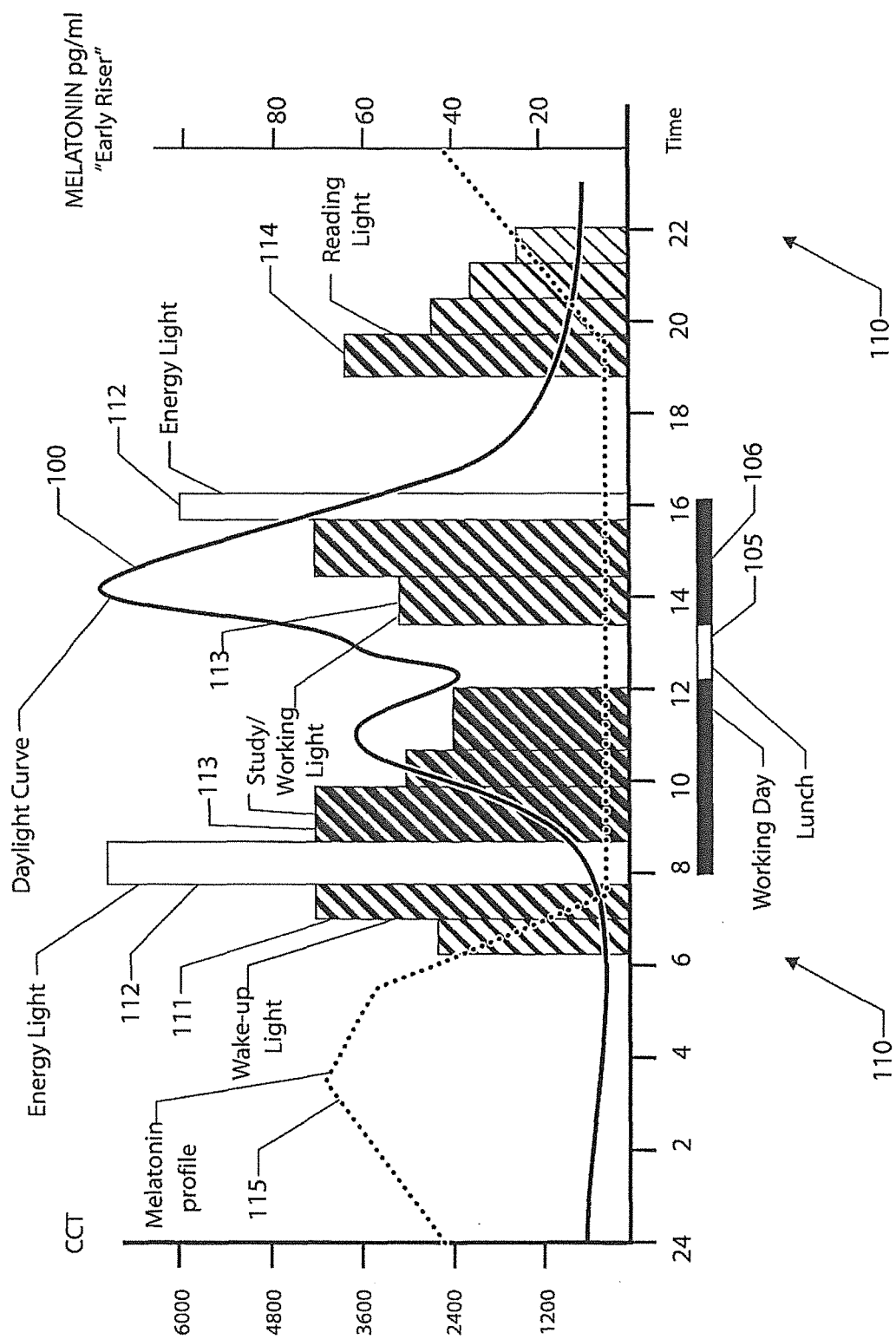
FIG. 12 shows an example of the outputs of a lighting system configured and loaded with biometric profiles about an A-type person.

FIG. 12 illustrates an example where the personal user is a chronotype A-person, (a "lark," early riser, or morning person).

The personal user's melatonin curve has been established and made available to the lighting system. The melatonin profile 115 is shown in the diagram and is shown to peak somewhere between 2:00 and 4:00 decreasing to a minimum around the time of awakening at 7:00.

06:30-07:45: The personal user is wakened by a stimulated spring sunrise profile that is made available by compensating the actual January sunrise. This is done by measuring the background light with the light sensor and comparing this to a stored profile of a spring sunrise and calculating needed values for output in terms of light intensity and CCT. These correction values are used to control a lamp in the sleeping room to gradually increase the light intensity and CCT, as shown by the wake-up light 111 in the figure, and to peak at a preset wake-up time just before 8:00.

07:45-08:45: The personal user gets, by way of choice or by preloaded instruction, a boost of energy light 112 to fully wake-up and to stop the melatonin production.

08:45-12:00: The personal user is working with a laptop with a screen that is used as a light source and which CCT is controlled by calculated outputs from the computational unit and based on background light, as from the daylight curve 100, characteristics measured by the light sensor.

12:00-13:30: The lighting system is off during and just after the lunch 106.

13:30-15:45: The personal user is after lunch working in an office with a stationary computer with a screen that is used as a light source and which CCT is controlled by calculated outputs from the computational unit based on the background light. See the daylight curve 100, as measured by the light sensor. The resulting study or work light 113 is seen to increase from a CCT of about 2500° K to 4500° K to maintain the personal user's energy level for a steady and productive work.

15:45-16:15: The personal user will be attending a meeting and voluntarily takes a boost of energy light 112 with a CCT of about 6000° K to be energized for the meeting.

16:15-18:45: The lighting system is off during the meeting and subsequent outdoor activities during the afternoon.

18:45-22:00: The personal user is at home and the light source is the installed lamps. The light sensor measures the background light, and the computational means calculates an output that results in a reading light 114 with a CCT of about 4000° K that will initiate the production of melatonin and decrease gradually to about 1500° K just before preparing bedtime at 22:00, thereby helping the personal user to get the "natural" A-type person rhythm and a rhythm that is in sync with a given working day and thereby extending the performance of the personal user and optimizing the personal users output.

Figure 13:
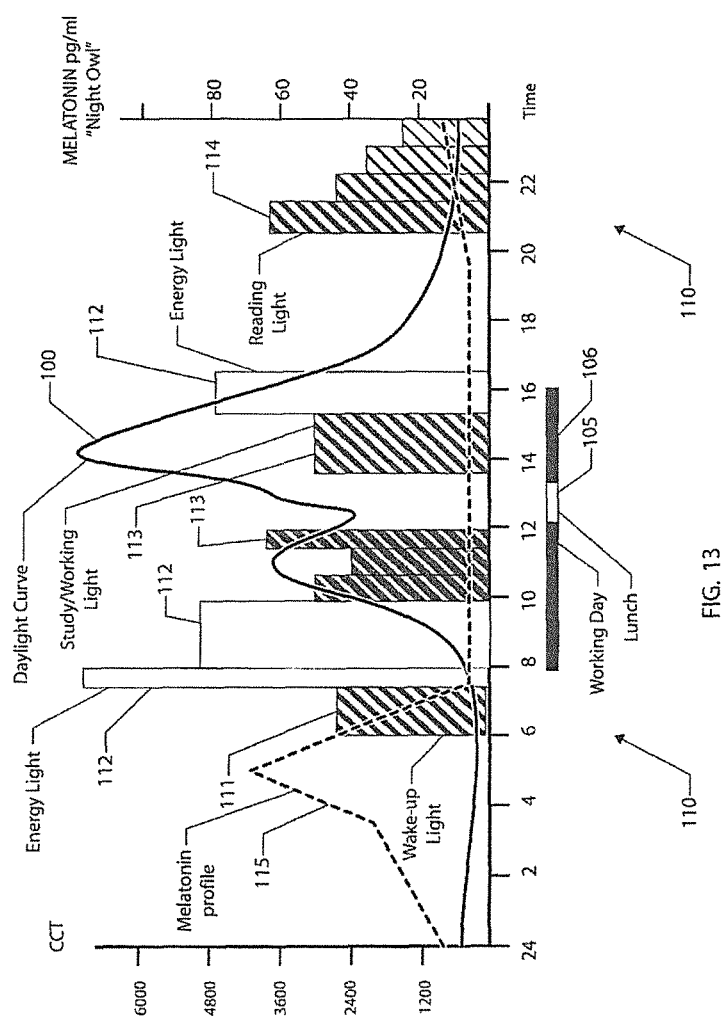
FIG. 13 shows an example of the outputs of a lighting system configured and loaded with biometric profiles about a B-type person.

FIG. 13 illustrates an example on the same day and with the same work schedule and daily program, as well as physical settings with rooms and computers as in the example with the A-type person illustrated in FIG. 12. However, in this example, the personal user is a B-type person (a "night owl" or evening person). Again the personal user's melatonin profile 115 is provided in the lighting system. The personal user's melatonin profile peaks at around 5:00, which is later than for the A-type person type in the example in FIG. 12.

06:00-07:45: A more steady and constant wake-up light 111 with a CCT of about 2500° K is provided to adjust the melatonin level, but at the same time allow the personal user to get the required sleep. The personal user is awakened at 7:45, were the light source is the lamp in the room controlled via the computational unit to light with bluish energy light 112 with a CCT of around 6500° K to abruptly stop the melatonin production and to significantly lower the melatonin level.

07:45-10:00: Likewise, when the personal user is at work, the laptop with the screen being the light source gives a steady and relatively cold and bluish energy light 112 with a CCT of around 5000° K for a period to bring the melatonin level to its minimum and to energize the personal user.

10:00-12:00: This is followed by a period of controlled light emission form the laptop screen, where the study or working light 113 varies according to the background light determined by the daylight curve 100.

12:00-13:30: The lighting system is off during and just after the lunch 106.

13:30-15:00: During this period the personal user is working on computer which screen emits a study or working light 112 with a CCT of about 3000° K to adjust the background light.

15:30-16:30: The personal user will be attending a meeting and voluntarily takes a boost of energy light 112 with a CCT of about 4700° K, which is lower than for the A-type person, so as not to get "too" energized and thereby unnaturally extend the day.

16:30-18:45: The lighting system is off during outdoor activities during the afternoon.

18:45-20:30: The lighting system gives a null-output in the evening since the background light does not need to be adjusted.

20:30-24:00: The reading light 114 is on and adjusts the background light to prepare the personal user for sleep and to adjust the CCT to initiate the production of melatonin.

Figure 14:
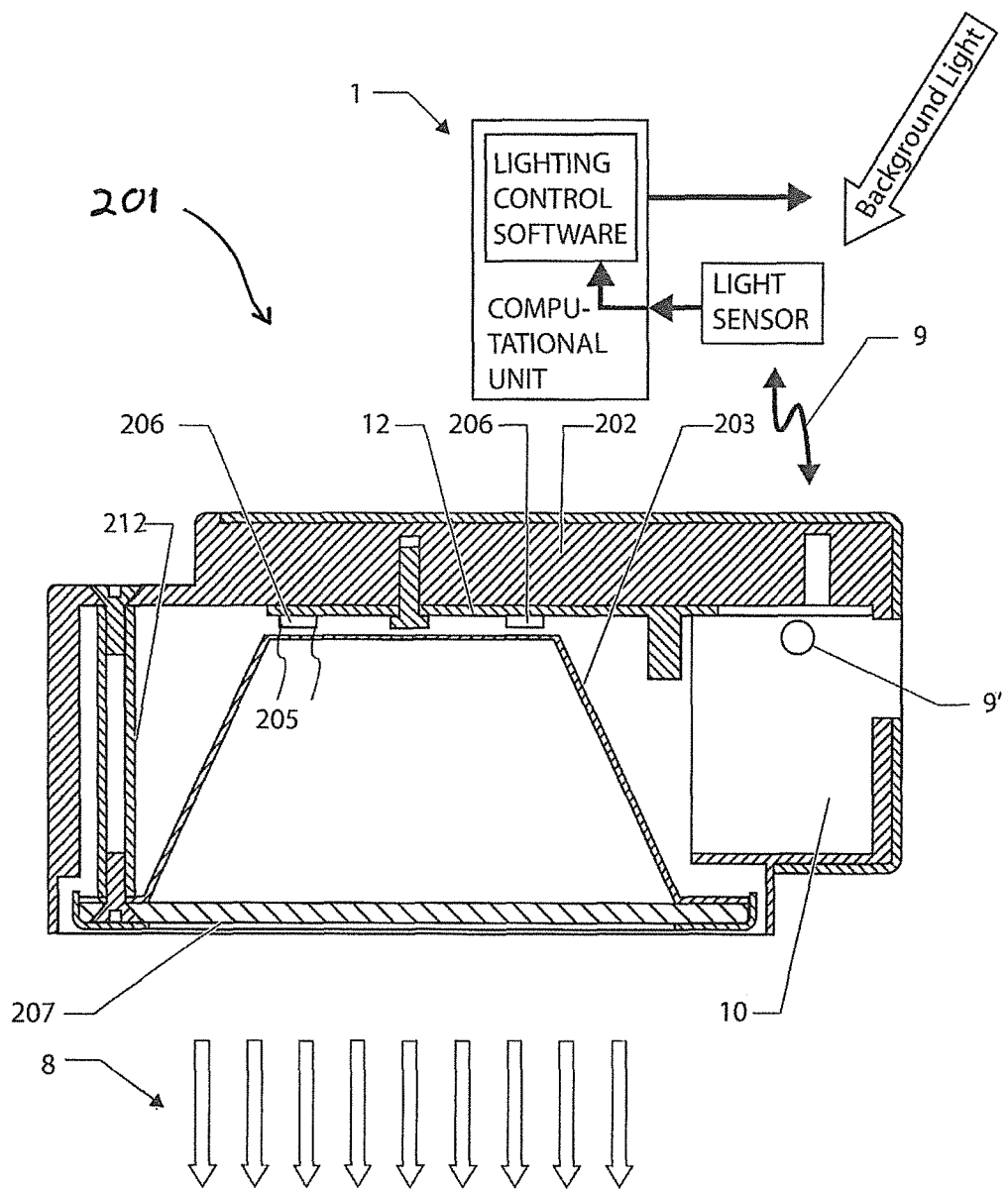
FIG. 14 shows an embodiment of a lamp with a light source, a reflector and a control unit, in accordance with the present disclosure.

FIG. 14 shows a lamp 201 with a housing 202 holding a reflector 203, a light source 12 with a plurality of light emitters 205 (here Light Emitting Diodes [LED's]) that are here arranged in a group of LEDs 206, and a diffuser 207 all configured to emit light 8. Furthermore, the housing 202 is configured to hold a light control unit 10 with a connector 9' for communicating with a light control unit 10 (only shown schematically in this figure). In this embodiment there is a spacer 212 for adjusting the distance of the diffuser 207 to the light source 12.

Figure 15A:
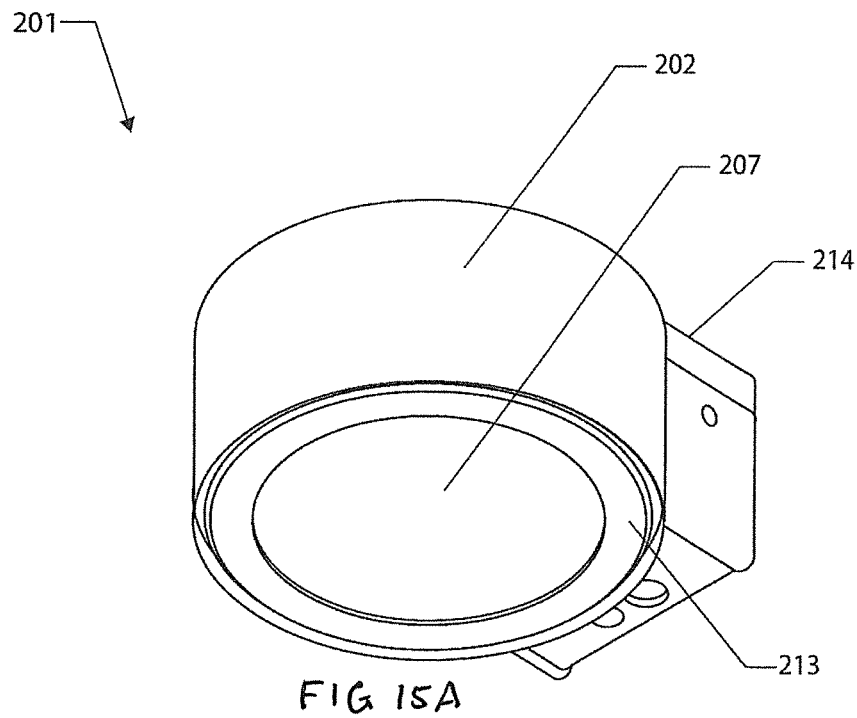
FIG. 15A shows a perspective view an embodiment of a lighting system in accordance with the present disclosure, with a housing and a cooler, taken from the bottom of the housing.
Figure 15:
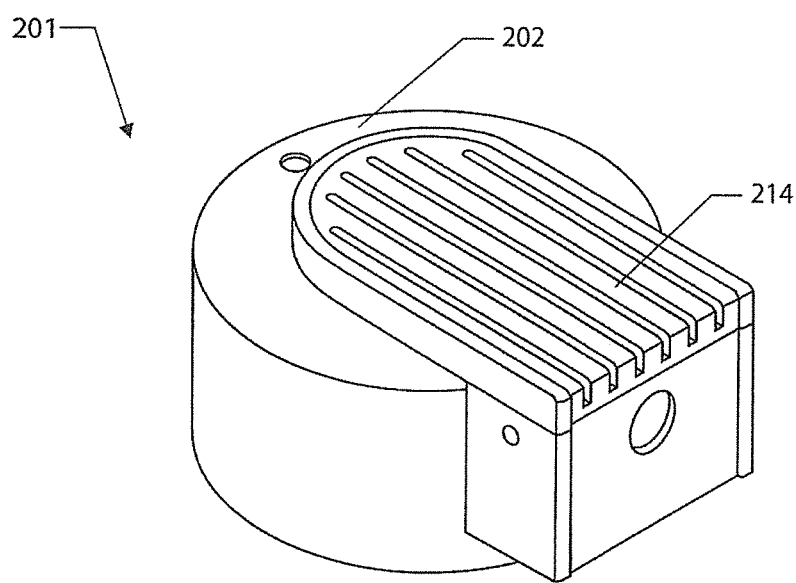
FIG. 15B shows a perspective view of the embodiment of FIG. 15A, taken from the top of the housing.

FIGS. 154 and 15B show an embodiment of a lamp 201 in two different perspective views. The housing 202 is shown with the diffuser 207 sealed by a cover 213 that ensures that ensures that no "false" light escapes. In a particular embodiment the cover 213 also supports the diffuser 207, the position of which is controlled by the spacer 212 (not seen in this figure). Furthermore a cooling element 214 is seen. As such, it is seen that the appearance of the lamp 201 is as any other conventional lamps, which, in this embodiment, may include side mounts.

Figure 16:
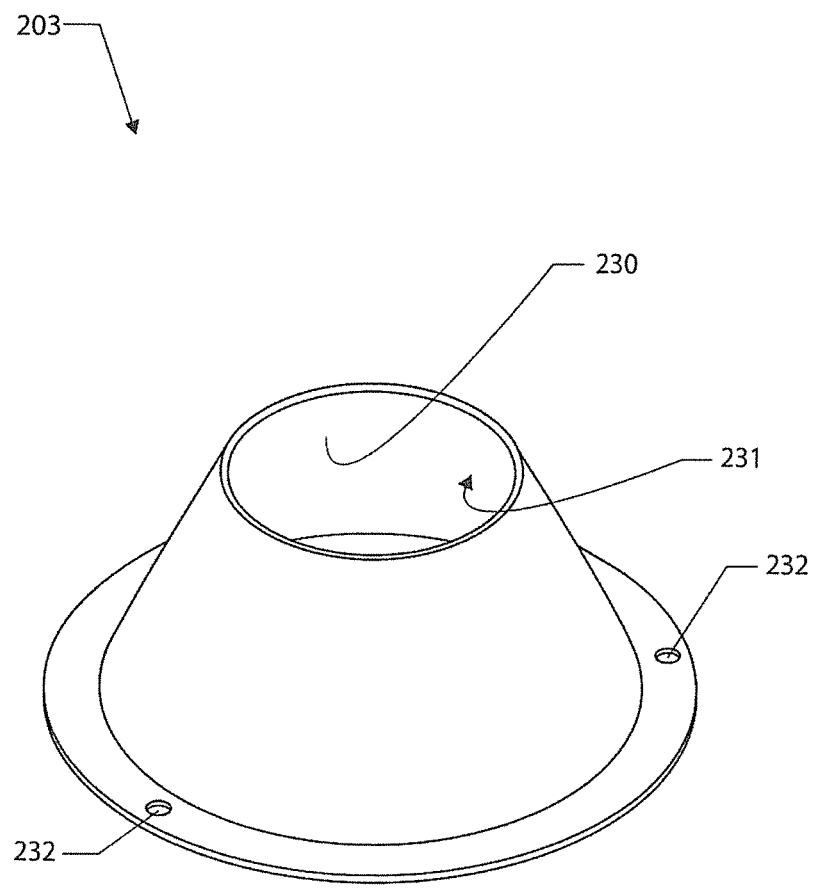
FIG. 16 shows a view of a reflector with a coating in accordance with the present disclosure.

FIG. 16 shows a perspective view of an embodiment of a reflector 203. The reflector has a reflector side 230. In this embodiment the reflector side 230 is coated with a reflector coating 231. The reflector coating is in this embodiment a barium sulphate-based coating with a so-called "avian white" characteristic. The reflector 203 has mounting means 232 for mounting the reflector 203 to the housing 202.

Figure 17:
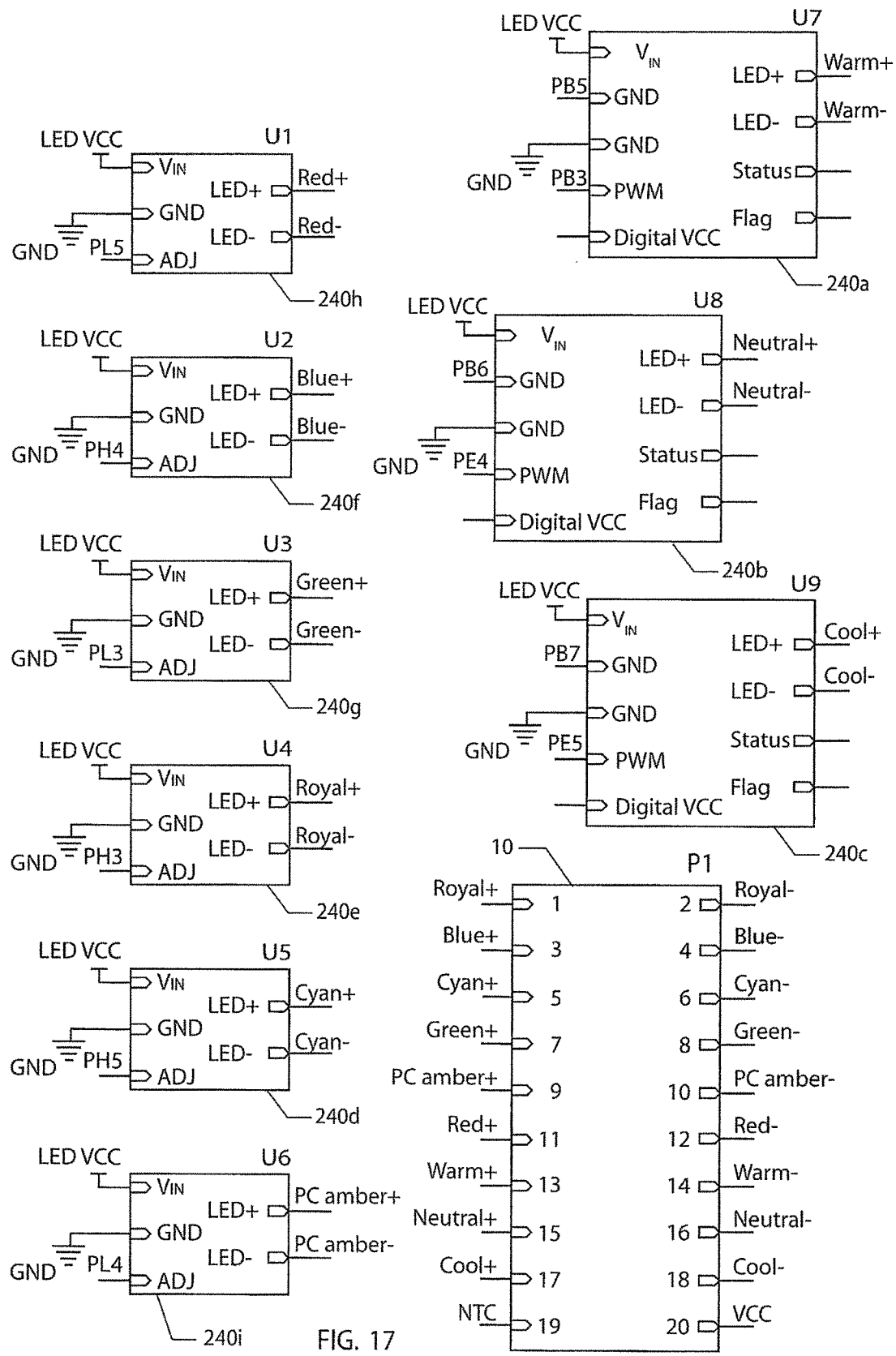
FIG. 17 shows a schematic view of drivers from the control unit to individual light emitters in accordance with the present disclosure.

FIG. 17 shows light emitter drivers 240 for light emitters 205 or a plurality of coupled light emitters 205. The light emitter drivers 240 are controlled by a light control unit 10.

In the particular embodiment shown there is:
 a light emitter driver 240a for driving at least one Warm White light emitting diode 205a; such as the LED from Cree Inc. with reference XP-E bin: XPEHEW-H1-8A2-G3-G-01 having a CCT between 2600° K-3700° K;
 a light emitter driver 240b for driving at least one Neutral White light emitting diode 5b; such as the LED from Cree Inc. with reference XP-E bin: XPEHEW-L1-5C2-Q5-G-01 having a CCT between 3700° K-5000° K;
 a light emitter driver 240c for driving at least one Cold White light emitting diode 205c; such as the LED from Cree Inc. with reference XP-E bin: XPEHEW-L1-2B0-R4-F-01 having a CCT between 5000° K-10,000° K;
 a light emitter driver 240d for driving at least one Cyan light emitting diode 205d; such as the LED from Phillips Inc. with reference Rebel bin: LXML-PE01-0070 having a DWL between 490-520 nm;
 a light emitter driver 240e for driving at least one Blue 460 nm light emitting diode 205e; such as the LED from Cree Inc. with reference XP-E Bin: XPEBLU-L 1-0000-00Y02 having a DWL between 450-465 nm;
 a light emitter driver 240f for driving at least one Blue 470 nm light emitting diode 205f; such as the LED from Cree Inc. with reference XP-E Bin: XPEROY-L 1-0000-00A01 having a DWL between 465-485 nm;
 a light emitter driver 240g for driving at least one Green light emitting diode 205g; such as the LED from Cree Inc. with reference XP-E Bin: XPEGRN-L1-0000-00B02 having a DWL between 520-535 nm;
 a light emitter driver 240h for driving at least one Red light emitting diode 205h; such as the LED from Cree Inc. with reference XP-E Bin: XPERED-L1-0000-00301 having a DWL between 620-630 nm; and
 a light emitter driver 240i for driving at least one Amber light emitting diode 205i; such as the LED from Phillips Inc. with reference Rebel bin: LXM2PL01-0090-CT1 having a DWL between 588-592 nm.

The light emitting diodes 205a, . . . , 205i are not shown, but are implied by the drivers. Likewise the connections between the light control unit 10 and the drivers are not shown.

A person skilled in the art will take this set-up as well as the indicated wavelength ranges as a starting point and by simple experimentation be able, by adjustment and slight variations in wavelength, to achieve the desired result without using the exact same manufacturer or model.

Figure 18:
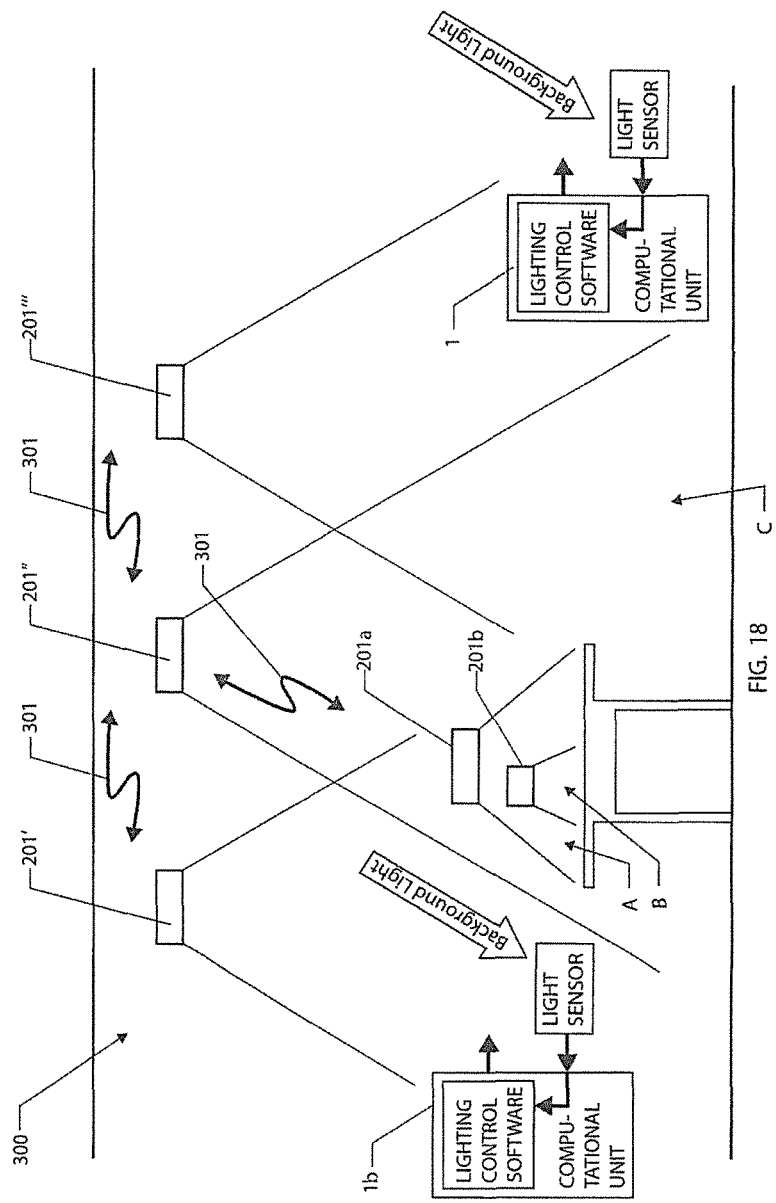
FIG. 18 shows an embodiment of multiple lamps arranged to light a room in different zones and communicating with multiple lighting systems in accordance with the present disclosure.

FIG. 18 shows a lamp network 300 of a plurality of lamps 201. Each lamp 201 has a connection to a wireless network 301 that can be a standard wireless network with a standard protocol and/or frequency or a private wireless network with a proprietary protocol and/or frequency configured to communicate between a lighting system 1. The figure exemplifies a lamp network 300 with three lamps 200', 201", 20'" placed in a ceiling, a table hung lamp 201a, and a desk lamp 201b, each lamp according to the device, system and method. The five lamps illuminate an area dividable into zones. In this case the area is divided into three zones A, B, and C.

In this particular embodiment, a lighting system 1 controls zone C by primarily regulating lamp 201'", to a lesser degree lamp 201", and to an even lesser degree lamp 201'; and a lighting system 1b controls zone B by primarily regulating lamp 201b, to a lesser degree lamp 201a, and to an even lesser degree lamps 201', 201", and 201'". Zone A is left uncontrolled, but naturally dependent on the control of zone B and C. This embodiment is only an example, and a person skilled in the art will only find it natural to explore other configurations according to the area at hand.

Figure 19:
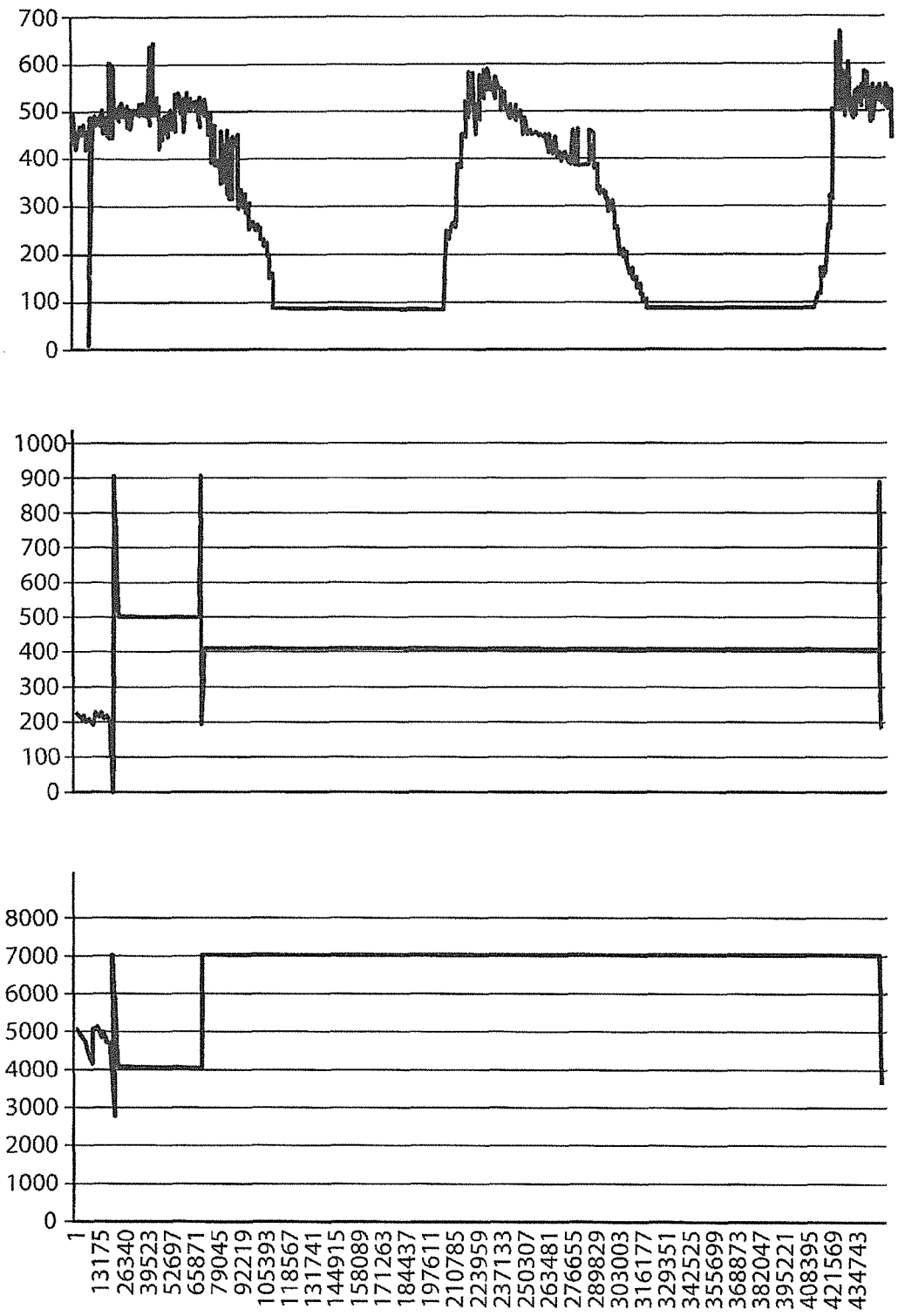
FIG. 19 shows time series of light intensity measured by the light sensor, light emitted from the lamp, and the color temperature of the light from the lamp, as in an embodiment of the present disclosure.

Finally. FIG. 19 shows a subset of data from an embodiment of the present disclosure, as collected, processed, and outputted for a female, who has pre-selected a chronotype suitable for an evening person. The top curve shows a scaled (1-1024) measure of light intensity as measured by a light sensor in an area or zone similar to zone B from FIG. 18 and in a room with windows. A lamp according to an embodiment of the present disclosure is placed similar to 201b in FIG. 18.

The time series covers a time period from a Friday morning to a Sunday morning and the variation in the sunlight over the days is clearly observed. Spikes in the data over the period come from turning on lights in the room and the lamp according to the present disclosure.

The middle curve shows the light intensity from the lamp as regulated by the lighting system automatically during the Friday morning and manually (boosts) shown as spikes. From Friday afternoon and through the weekend, the lamp was left on at a fixed intensity as also showing as a constant floor in the top curve after sunset.

For a short period Friday morning, the system was turned off.

The bottom curve shows the color temperature of the lamp as regulated by the lighting system.

It is observed that the system is configured to be able to regulate intensity as well as color temperature continuously. The two small declines in the color temperature and the corresponding decline in intensity are to maintain a substantially constant light intensity and color temperature in the working area around the lamp.

A first peak in intensity and increase in color temperature to about 7000° K is seen and caused by a request by the user to get a boost by a quantum of "intense blue light". For the remaining period over the weekend, the lamp is switched on at a constant intensity/color temperature and working a safety light with low energy consumption.

The above description can be summarized in the following points:

1. A lighting system (1) for initiating change of a mammal's (70) circadian state or well-being state, comprising:
 at least one computational unit (2) with a memory, a processor, at least one input (3) and at least one output (4); and
 at least one light sensor (5) with spectral and luminosity sensitivity and means for providing information through a connection (6) to said least one input (3) of the computational unit (2), which computational unit (2) has computational means (7) that are arranged for collecting, storing, and processing data from at least the light sensor (5) providing operational information (77) and comparing said operational information (77) with state information (76) about the mammal's (70) circadian state or well-being state and which computational means (7) compares the operational information (77) and the state in-formation (76) for activating means for generating at least one output signal (4) on at least one connector (9) for communicating with and controlling at least one light source (12, 201), and which computational unit (2) is configured to calculate and least one output signal (4) configured to output the setting of at least one light source (12) or lamp (201) to a color temperature range between 2700° K-7000° K, an intensity range between 10 to 1000 lumens, and a Ra-index greater than 92 at all values of color temperature and intensity.

2. A lighting system (1) according to point 1, characterized in that said lighting system (1) further comprises at least one user interface (20) with a connection to of the computational unit (2) for making personal data (21) available to the computational means (7).

3. A lighting system (1) according to any of points 1 to 2, characterized in that said lighting system (1) further comprises at least one computational interface for connecting to at least one second computational unit for retrieving and storing information.

4. A lighting system (1) according to any of points 1 to 3, characterized in that said lighting system (1) further comprises at least one biometrical sensor unit (31) with a connection to the computational unit (2) for providing biometric data (30) to the computational means (7).

5. A lighting system (1) according to any of points 1 to 4, characterized in that said lighting system (1) further comprises at least one activity sensor unit (41) for providing activity data (40) to the computational means (7).

6. A lighting system (1) according to any of points 1 to 5, characterized in that said lighting system (1) to the computational unit (2) via a connection further comprises at least one additional sensor or detector unit being a unit such as a time detector or unit (51), a location detector or unit (52), a work schedule detector or unit (53), a sleep pattern detector or unit (54), a daylight detector or unit (55), a mood detector or unit (56), a health detector or unit (57), a date detector or unit (58), an mammal energy detector or unit (59), and/or a connection detector or unit for receiving data or information from an unlisted unit via a protocol.

7. A lighting system (1) according to any of the points 1 to 6, characterized in that said units or detectors (5, 20, 31, 41, 51, 52, 53, 54, 55, 56, 57, 58, 59) are connected to the computational unit (2) or said units or detectors (5, 20, 31, 41, 51, 52, 53, 54, 55, 56, 57, 58, 59) are embedded in the computational unit (2).

8. A lamp (12, 201) emitting light (8), comprising a housing (202) configured to hold a reflector (203) configured to reflect and/or direct light from a least one light source (12) through a diffuser (207); wherein said lamp (201) further comprises a light control unit (10) with at least one connector (9') for communicating with and receiving regulating information from a lighting system (1) according to any of points 1 to 7 and configured to vary at least one light source (12) so the light (8) emitted from the lamp (201) has a color temperature range between 2700° K-7000° K, an intensity range between 10 to 1000 lumens, and a Ra-index greater than 92 at all values of color temperature and intensity.

9. A lamp (201) according to point 8, characterized in that the light source (12) comprises a plurality of light emitters (205), preferably light emitting diodes or LEDs.

10. A lamp (1) according to any of points 8 to 9, characterized in that light emitters (205) in the light source (12) are configured on the basis of color mixing of chromaticity binning using a plurality of bins, individually or a pre-selected plurality of bins formed to generate a warm white, neutral white, or cool white or combinations thereof.

11. A lamp (12) according to any of points 8 to 10, characterized in that the light source (12) comprises:
at least one red, at least one blue, at least one green, at least one Royal blue, at least one cyan, at least amber light emitters in combination with at least a white light emitter; or
comprises at least one red, at least one green, and at least blue light emitters; or comprises at least one white/yellow and phosphor converted light emitters in combination with at least one blue, and at least a first and a second red light emitter combination with at least a white light emitter;
wherein said least one white light emitter comprises:
at least one emitting warm white light emitting diode having a CCT between 2600° K-3700° K, at least one emitting neutral white light emitting diode having a CCT between 3700° K-5000° K, and at least one emitting cold white light emitting diode having a CCT between 5000° K-10,000° K; or
at least one white light emitter has a CCT between 2700° K or 7000° K.

12. A lamp (201) according to point 11, characterized in that, the light control unit (10) is configured to vary each light emitter (205) by means of a lookup table, one or more programmed functions, or an interpolation of said lookup table or one or more programmed functions or both.

13. A lamp (201) according to any of points 8 to 12, characterized in that the lamp (201) further includes at least a second connector for communicating regulating information via a standard wireless network (301) with a standard protocol such as CAN, a private wireless lamp network (301) for communicating with at least one other lamp, or a wired network with a standard protocol such as CAN.

14. A kit of at least one lamp (201) according to any of points 8-13 and at least one lighting system (1) according to any of points 1-7.

15. A network of lamps (300) comprising a plurality of lamps (201) according to any of points 8-13 and at least one lighting system (1) according to any of points 1-7, characterized in that said lamps (201) and least one lighting system (1) are configured in zones (A, B, . . . ), each zone (A, B, . . . ) being controlled or regulated by at least one lamp (201) and at least one lighting system (1).

16. A method for initiating change of a mammal's (70) circadian state or well-being state using at least one lamp (201) according to any of points 8-13 and at least one lighting system (1) according to any of points 1-7, the method comprising:
measuring the intensity and the chromaticity of light surrounding (71, 8, 13) the mammal (70) and providing the measuring as light data (83);
collecting, storing, and processing measured light data and making operational information (77) thereof; and
generating an output signal (4) for initiating change of the mammals (70) surroundings.

17. A method according to point 16 further comprising:
retrieving or storing data about a mammals (70) circadian state or well-being state and making state information (76) thereof; and
comparing the operational information (77) and the state information (76) before generating an output (4) based on the comparison.

18. A method according to point 16 or 17 further comprising varying at least one light source's (12) luminosity or chromaticity, which least one light source (12) is present in the surroundings (71) of the mammal (70), thereby generating an output signal (4) for initiating a change of the mammals (70) surrounding (71) light conditions (13).

PARTIAL ITEM LIST 1000 lighting system
1002 time detector or unit
1004 user interface
1006 computational unit
1008 lamp
1010 current time
1012 type parameter
1014 gender parameter
1016 age parameter
1018 first function
1020 second function
1022 output control parameter
1024 first peak
1026 first maximum
1027 first time of the day
1028 first full width at half maximum
1030 second peak
1032 second maximum
1033 second time of the day
1034 second full width at half maximum
1035 first base function $T_0(t)$
1036 first type of person male
1038 first type of person female
1040 second type of person male
1042 second type of person female
1044 first range of local time
1045 colour temperature base level
1046 first depression
1048 first minimum
1049 third time of the day
1050 fifth peak
1052 fifth maximum
1053 seventh time of the day
1054 fifth full width at half maximum
1056 third peak
1058 third maximum
1059 fourth time of the day
1060 third full width at half maximum
1062 fourth peak
1064 fourth maximum
1065 fifth time of the day
1066 fourth full width at half maximum
1068 second depression
1070 second minimum
1071 sixth time of the day
1072 fourth base function $I_0(t)$
1074 30 year old
1076 60 year old
1078 intensity base level
1080 second and third range of local time
1082 fifth base function $c_{age}(z)$

What is claimed is:

1. A method for providing an output control parameter associated with a specific person for controlling a light output of a lamp, the light output being characterized by a color temperature, and the control parameter comprising a color temperature control parameter for controlling the color temperature of the light output, the method comprising:
(a) providing a current time parameter representing the current local time of the day;
(b) providing a type parameter representing one of a first person type and a second person type;
(c) providing a gender parameter representing one of a male person and a female person; and
(d) in a first alternative providing a first function comprising:
(i) as an input, a first variable representing the local time, a second variable representing the type parameter, and a third variable representing the gender parameter; and
(ii) a range of color temperature control parameters as an output;
the first function defining a first peak and a second peak of the range of color temperature control parameters with respect to the first variable, the first peak having a first maximum at a first time of the day and a first full width at half maximum of at least 30 minutes, the second peak having a second maximum at a second time of the day that is after the first time of the day and a second full width at half maximum of at least 30 minutes;
the first function providing at a fixed value of the third variable an output representing a lower color temperature at the first time of the day for the first type of person than for the second type of person, and an output representing a higher color temperature at the second time of the day for the first type of person than for the second type of person, and
the first function further providing at a fixed value of the second variable an output representing a lower color temperature at the first time of the day and the second time of the day for a male person than for a female person; and
(e) in a second alternative providing a first function representing:

$$T(t,x,y)=(T_0(t)-T_b)\cdot c_{type}(x)\cdot c_{gender}(y)+T_b,$$

where t is a first variable representing the local time, x is a second variable representing the type parameter, and y is a third variable representing the gender parameter;
wherein the first, second and third variables constitute an input for the first function, $T(t, x, y)$ is the output of the first function and covers a range of temperature control parameters, $T_0(t)$ is a first base function of the first variable t and defines a first peak and a second peak of the range of color temperature control, the first peak having a first maximum at a first time of the day and a first full width at half maximum of at least 30 minutes, the second peak having a second maximum at a second time of the day that is after the first time of the day and a second full width at half maximum of at least 30 minutes, $c_{type}(x)$ is a second base function of the second variable x and provides an output corresponding to a lower color temperature at the first time of the day for the first type of person than for the second type of person, and an output representing a higher color temperature at the second time of the day for the first type of person than for the second type of person, $c_{gender}(y)$ is a third base function of the third variable y and provides an output corresponding to a lower color temperature at the first time of the day and the second time of the day for a male person than for a female person, and $T_b$ is a color temperature base level that is a positive constant for all values of the first, second, and third variables; and (f) in both the first and the second alternatives, inputting into the first function the current time parameter as the first variable, the type parameter as the second variable, and the gender parameter as the third variable to yield the color temperature control parameter as the output from the first function.

2. The method of claim 1, wherein, in the first alternative, the first function defines a color temperature base level representing a positive constant color temperature over a first range of the local time, the color temperature is independent of the second variable and the third variable over the first range, the first full width at half maximum represents the width of the first peak at a color temperature corresponding to the mean of the color temperature of the first maximum and the color temperature at the color temperature base level, and the second full width at half maximum represents the width of the second peak at a color temperature corresponding to the mean of the color temperature of the second maximum and the color temperature at the color temperature base level.

3. The method of claim 1, wherein, in the second alternative, the first base function $T_0(t)$ is zero over a first range of the local time, the first full width at half maximum represents the width of the first peak at the middle between the first maximum and $T_b$, and the second full width at half maximum represents the width of the second peak at the middle between the second maximum and $T_b$.

4. The method of claim 1, wherein, in the first alternative, the first function defines a first depression between the first peak and the second peak at fixed values of the second and third variables, the first depression has a first minimum at a third time of the day and the first function provides an output at the third time of the day that is the same for all values of the second variable and the third variable.

5. The method of claim 1, wherein, in the second alternative, the first base function $T_0(t)$ defines a first depression between the first peak and the second peak, the first depression has a first minimum at a third time of the day, the second base function $c_{type}(x)$ provides an output at the third time of the day that is the same for all values of the second variable x, and the third base function $c_{type}(x)$ provides an output at the third time of the day that is the same for all values of the third variable y.

6. The method of claim 1, wherein the first time of the day is before noon according to the local time.

7. The method of claim 1, wherein second time of the day is after noon according to the local time.

8. The method of claim 1, wherein the light output is further characterized by an intensity, wherein the control parameter further comprises an intensity control parameter for controlling the intensity of the light output, and wherein the method further comprises:
(a) in the first alternative, providing a second function comprising:
(i) a fourth variable representing the local time;
(ii) a range of intensity control parameters as output;
(iii) the second function defining a third peak and a fourth peak of the range of intensity control parameters;
(iv) the third peak having a third maximum at a fourth time of day and a third full width at half maximum of at least 30 minutes; and
(v) the fourth peak having a fourth maximum at a fifth time of the day that is after the fourth time of the day and a fourth full width at half maximum of at least 30 minutes; and (b) inputting into the second function the current time parameter as the fourth variable to yield the intensity control parameter as the output from the second function.

9. The method of claim 8, wherein, in the first alternative, the second function defines an intensity base level representing a positive constant intensity over a second range of the local time, the third full width at half maximum represents the width of the third peak at an intensity corresponding to the mean of the intensity of the third maximum and the intensity at the intensity base level, and the fourth full width at half maximum represents the width of the fourth peak at an intensity corresponding to the mean of the intensity of the fourth maximum and the intensity at the intensity base level.

10. The method of claim 8, wherein, in the first alternative, the second function is constant over a third range of the local time at a fixed value of the fifth variable, the first function defines a fifth peak having a fifth maximum at a seventh time of day and a fifth full width at half maximum of at least 15 minutes, and the third range of the local time is after at least one of the second time of the day and the fourth time of the day and comprises the seventh time of the day.

11. The method according to claim 8, wherein, in the second alternative, the second base function is constant over a third range of the local time, the first base function defines a fifth peak having a fifth maximum at a seventh time of day and a fifth full width at half maximum of at least 15 minutes, and the third range of the local time is after the second time of the day and comprises the seventh time of the day.

12. The method of claim 1, wherein the light output is further characterized by an intensity, wherein the control parameter further comprises an intensity control parameter for controlling the intensity of the light output, and wherein the method further comprises:
(a) in the second alternative, providing a second function representing $I(t)=I_0(t) \cdot c$,
where t is a fourth variable representing the local time and the fourth variable is an input for said second function, I(t) is the output covering a range of intensity control parameters, $I_0(t)$ is a fourth base function of the fourth variable t and defines a third peak and a fourth peak of the range of color temperature control, the third peak having a third maximum at a fourth time of day and a third full width at half maximum of at least 30 minutes, the second peak having a fourth maximum at a fifth time of the day that is after the fourth time of the day and a fourth full width at half maximum of at least 30 minutes, and c is a correction factor; and
(b) inputting into the second function the current time parameter as the fourth variable to yield the intensity control parameter as the output from the second function.

13. The method of claim 12, wherein in the second alternative the fourth base Function $I_0(t)$ is approximately equal to an intensity base level over a second range of the local time where the intensity base level is a constant, the third full width at half maximum represents the width of the third peak at the middle between the third maximum and the intensity base level, and the fourth full width at half maximum represents the width of the fourth peak at the middle between the fourth maximum and the intensity base level.

14. The method of either of claim 8 or 12, wherein, in the first alternative, the second function defines a second depression between the third peak and the fourth peak, the second depression having a second minimum at a sixth time of the day.

15. The method of either of claim 8 or 12, wherein, in the second alternative, the fourth base function $I_0(t)$ defines a second depression between the third peak and the fourth peak, the second depression having a first minimum at a sixth time of the day.

16. The method of either of claim 8 or 12, wherein the first time of the day and the fourth time of the day are the same time of the day, wherein the second time of the day and the fifth time of the day are the same time of the day, and wherein the third time of the day and the sixth time of the day are the same time of the day.

17. The method of either of claim 8 or 12, wherein the method further comprises:
   providing an age parameter representing an age of a person, wherein, in the first alternative, the second function further comprises:
      a fifth variable representing the age parameter as input, the second function providing, at a fixed value of the fourth variable, an output that increases monotonically with the fifth variable; and
   inputting into the second function the age parameter for the specific person as the fifth variable in addition to the current time parameter as the fourth variable to yield the intensity control parameter as the output from the second function.

18. The method of claim 17, wherein, in the first alternative, the second function provides, at a fixed value of the fourth variable, an output that increases exponentially with the fifth variable.

19. The method of claim 17, wherein, in the second alternative, the fifth base function $c_{age}(z)$ represents $c_{age}(z) = 1/(2^{(13/(z-25))})$, where the parameter z is in the unit of years.

20. The method of either of claim 8 or 12, wherein the method further comprises:
   providing an age parameter representing an age of a person, wherein, in the second alternative, the second function further represents $I(t, z) = I_0(t) \cdot c_{age}(z)$, where t is the fourth variable representing the local time, z is a fifth variable representing the age parameters, and the fourth and fifth variables constitute the input for the second function, $I(t, z)$ is the output of the second function and covers the range of intensity control parameters, $I_0(t)$ is the fourth base function of the fourth variable t, and $c_{age}(z)$ is a fifth base function of the fifth variable z, the fifth base function constituting the correction factor c and providing an output representing an intensity that increases monotonically with the age of the person; and
   inputting into the second function the age parameter for the specific person as the fifth variable in addition to the current time parameter as the fourth variable to yield the intensity control parameter as the output from the second function.

21. The method of claim 20, wherein, in the first alternative, the second function provides, at a fixed value of the fourth variable, an output that increases exponentially with the fifth variable.

22. The method of claim 20, wherein, in the second alternative, the fifth base function $c_{age}(z)$ represents $c_{age}(z) = 1/(2^{(13/(z-25))})$, where the parameter z is in the unit of years.

23. The method according to claim 12, wherein, in the first alternative, the second function is constant over a third range of the local time at a fixed value of the fifth variable, the first function defines a fifth peak having a fifth maximum at a seventh time of day and a fifth full width at half maximum of at least 15 minutes, and the third range of the local time is after at least one of the second time of the day and the fourth time of the day and comprises the seventh time of the day.

24. The method according to claim 12, wherein, in the second alternative, the second base function is constant over a third range of the local time, the first base function defines a fifth peak having a fifth maximum at a seventh time of day and a fifth full width at half maximum of at least 15 minutes, and the third range of the local time is after the second time of the day and comprises the seventh time of the day.

* * * * *